(12) United States Patent
Drake et al.

(10) Patent No.: US 10,159,834 B2
(45) Date of Patent: Dec. 25, 2018

(54) COMPACT IMPLANTABLE MEDICAL DEVICE AND DELIVERY DEVICE

(71) Applicant: Medtronic, Inc., Minneapolis, MN (US)

(72) Inventors: Ronald A Drake, St. Louis Park, MN (US); Kenneth C Gardeski, Plymouth, MN (US); Carla Pfeiffer, Anoka, MN (US); Kevin R Seifert, Forest Lake, MN (US); Lester O Stener, Hudson, WI (US); Matthew D Bonner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 156 days.

(21) Appl. No.: 15/416,282

(22) Filed: Jan. 26, 2017

(65) Prior Publication Data

US 2017/0209690 A1   Jul. 27, 2017

Related U.S. Application Data

(60) Provisional application No. 62/286,967, filed on Jan. 26, 2016.

(51) Int. Cl.
| | | |
|---|---|---|
| *A61N 1/05* | (2006.01) | |
| *A61N 1/368* | (2006.01) | |
| *A61N 1/372* | (2006.01) | |
| *A61N 1/375* | (2006.01) | |

(52) U.S. Cl.
CPC ......... *A61N 1/0573* (2013.01); *A61N 1/3688* (2013.01); *A61N 1/3756* (2013.01); *A61N 1/37205* (2013.01); *A61N 2001/058* (2013.01); *A61N 2001/0578* (2013.01)

(58) Field of Classification Search
None
See application file for complete search history.

(56) References Cited

U.S. PATENT DOCUMENTS

| | | |
|---|---|---|
| 3,814,104 A | 6/1974 | Irnich et al. |
| 4,103,690 A | 8/1978 | Harris |
| 6,055,457 A | 4/2000 | Bonner |

(Continued)

OTHER PUBLICATIONS (PCT/US2017/015066) PCT Notification of Transmittal of the International Search Report and the Written Opinion of the International Searching Authority, dated May 8, 2017, 12 pages.

(Continued)

*Primary Examiner* — Brian T Gedeon

(57) ABSTRACT

Methods and systems for positioning a leadless pacing device (LPD) in cardiac tissue are disclosed. A delivery device is employed that comprises a proximal end, a distal end and a lumen therebetween sized to receive the LPD. The LPD has a leadlet extending therefrom that includes a means to fixate the leadlet to tissue. The delivery device comprises an introducer to introduce the LPD into the lumen of the delivery device. The LPD is loaded in the distal end of the lumen of the delivery device. The leadlet extends proximally from the LPD while the fixation means extends distally toward the LPD. A LPD mover is configured to advance the LPD out of the delivery device. A leadlet mover is configured to advance the leadlet out of the lumen delivery device and cause the leadlet to engage with cardiac tissue.

29 Claims, 31 Drawing Sheets

(56) References Cited

U.S. PATENT DOCUMENTS

| | | |
|---|---|---|
| 6,738,672 B2 | 5/2004 | Schulman et al. |
| 6,823,217 B2 | 11/2004 | Rutten et al. |
| 7,082,336 B2 | 7/2006 | Ransbury et al. |
| 7,130,700 B2 | 10/2006 | Gardeski et al. |
| 7,331,922 B2 | 2/2008 | Mohl |
| 7,616,992 B2 | 11/2009 | Dennis et al. |
| 7,647,109 B2 | 1/2010 | Hastings et al. |
| 7,949,395 B2 | 5/2011 | Kuzma |
| 8,012,127 B2 | 9/2011 | Lieberman et al. |
| 8,262,672 B2 | 9/2012 | Neidert et al. |
| 8,478,431 B2 | 7/2013 | Griswold et al. |
| 8,532,790 B2 | 9/2013 | Griswold |
| 8,615,310 B2 | 12/2013 | Khairkhahan et al. |
| 8,634,912 B2 | 1/2014 | Bornzin et al. |
| 8,755,909 B2 | 6/2014 | Sommer et al. |
| 9,119,959 B2 | 9/2015 | Rys et al. |
| 9,155,882 B2 | 10/2015 | Grubac et al. |
| 9,414,857 B2 | 8/2016 | Wood et al. |
| 9,446,248 B2 | 9/2016 | Sheldon et al. |
| 9,526,522 B2 | 12/2016 | Wood et al. |
| 9,526,891 B2 | 12/2016 | Eggen et al. |
| 9,539,423 B2 | 1/2017 | Bonner et al. |
| 9,808,629 B2 * | 11/2017 | Steingisser ......... A61N 1/3756 |
| 2002/0095203 A1 | 7/2002 | Thompson et al. |
| 2004/0147973 A1 | 7/2004 | Hauser |
| 2006/0247753 A1 | 11/2006 | Wenger et al. |
| 2009/0082828 A1 | 3/2009 | Ostroff |
| 2011/0251661 A1 | 10/2011 | Fifer et al. |
| 2011/0270340 A1 | 11/2011 | Pellegini et al. |
| 2012/0172690 A1 | 7/2012 | Anderson et al. |
| 2012/0172892 A1 | 7/2012 | Grubac et al. |
| 2013/0110127 A1 | 5/2013 | Bornzin et al. |
| 2013/0253345 A1 | 9/2013 | Griswold et al. |
| 2014/0107723 A1 | 4/2014 | Hou et al. |
| 2014/0180306 A1 | 6/2014 | Grubac et al. |
| 2015/0039070 A1 | 2/2015 | Kuhn et al. |
| 2015/0051682 A1 | 2/2015 | Schmidt et al. |
| 2015/0094668 A1 | 4/2015 | Wood et al. |
| 2016/0059002 A1 | 3/2016 | Grubac et al. |
| 2016/0059003 A1 * | 3/2016 | Eggen ................. A61N 1/3756 606/129 |
| 2016/0096001 A1 * | 4/2016 | Eidenschink ....... A61M 25/008 606/129 |
| 2017/0028194 A1 * | 2/2017 | Bonner ................. A61N 1/057 |

OTHER PUBLICATIONS http://www.mana-tech.com/factsheets/HomerMammalok.pdf.
Medtronic model SELECTSURE™ 3830 manual, 2013, 20 pages.

* cited by examiner

COMPACT IMPLANTABLE MEDICAL DEVICE AND DELIVERY DEVICE

CROSS-REFERENCE TO RELATED APPLICATIONS

This application claims the benefit of U.S. Provisional Application No. 62/286,967, filed on Jan. 26, 2016. The disclosure of the above application is incorporated herein by reference in its entirety.

FIELD OF THE DISCLOSURE

The present disclosure pertains to delivery of implantable medical devices, and, more particularly, to delivery of relatively compact implantable medical devices.

BACKGROUND

Conventional implantable cardiac pacemakers typically include one or more medical electrical leads that deliver pacing pulses to cardiac tissue and sense the response thereto. Leads occasionally may have mechanical complications and/or MRI compatibility issues. Consequently, relatively compact implantable cardiac pacing devices have been developed that are able to deliver pacing pulses to cardiac tissues without leads. MICRA™, commercially available from Medtronic Inc., is one example of a compact implantable cardiac pacing device that is configured for implant in close proximity to a pacing site. Other microstimulators have been designed with short pacing leads referred to as leadlets. Exemplary microstimulators having leadlets or features thereof are shown in U.S. Pat. No. 7,949,395 B2 to Kuzma, US Patent Pregrant Publication No. 20040147973 A1 to Hauser, U.S. Pat. No. 7,082,336 B2 to Ransbury et al., U.S. Pat. No. 6,738,672 B2 to Schulman et al., U.S. Pat. No. 9,446,248 B2 to Sheldon et al., US Pregrant Publication No. 20110270340 A1 to Pellegrini et al., US Pregrant Publication No. 20090082828 A1 to Ostroff, U.S. Pat. No. 8,634,912 B2 to Bornzin, et al., U.S. Pat. No. 9,539,423, and U.S. Pat. No. 9,446,248 B2 to Sheldon et al. A need exists for improved delivery and fixation means for compact implantable cardiac pacing devices.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and.

SUMMARY

Figure 1:
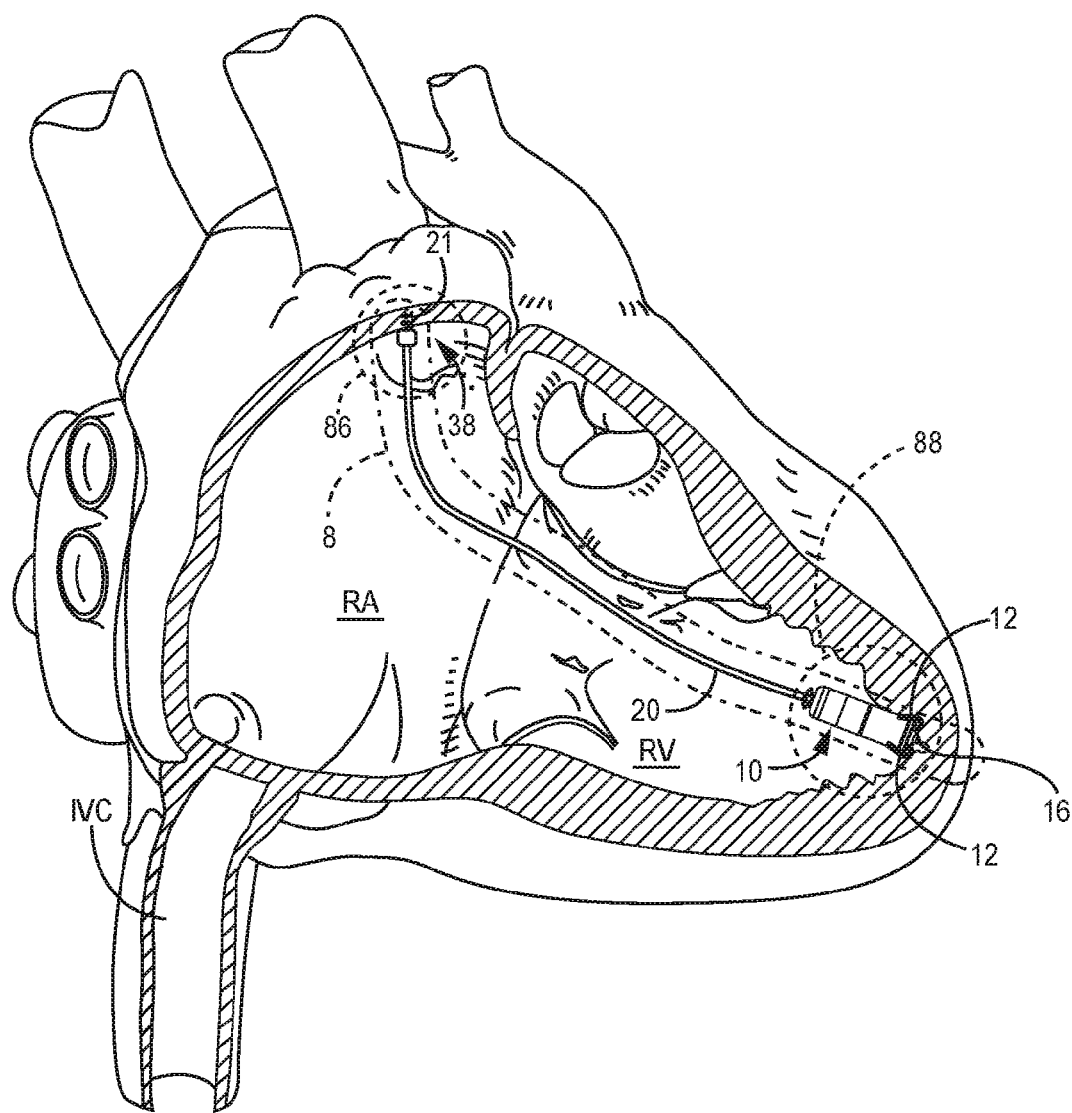
FIG. 1 is a schematic diagram showing an exemplary compact dual chamber intra-cardiac pacing device implanted in a heart.

One or more embodiments are directed to using a delivery device and method for deploying a compact dual chamber intra-cardiac pacing device within the heart. The compact dual chamber intra-cardiac pacing device comprises a leadlet pacing device (LPD) and a leadlet. The intra-cardiac pacing device is loaded into the lumen at the distal end of the delivery device. Loading the intra-cardiac pacing device into the delivery device requires the leadlet to extend proximally from the LPD while the leadlet fixation means (i.e. helix) extends distally toward the LPD. The delivery device is then positioned in close proximity to ventricular tissue (e.g. right ventricle (RV). The user engages a LPD mover that contacts the proximal end or rear of the LPD and causes the LPD to move in the distal direction out of the delivery device. During or after the LPD exits the distal end of the delivery device, the tines of the LPD deploy and attach to ventricular tissue. After the LPD is secured to tissue through the tines, the delivery device may be moved to allow the leadlet to be in close proximity to atrial tissue. The leadlet is then advanced out of the distal end of the delivery device using a leadlet mover. The leadlet mover looks like a tuning fork with two prongs extending from a base. The two prongs are configured to engage and counter-rotate the leadlet free end (i.e. near the helical tip).

Counter-rotation causes the leadlet to wind around the leadlet mover thereby creating stress in the leadlet body. Once the helical tip contacts the atrial tissue, the leadlet is allowed to unwind and/or is rotated by the leadlet mover. Unwinding the leadlet causes the helical tip to attach to the atrial tissue while releasing stress in the leadlet body. The compact dual chamber intra-cardiac pacing device is electrically tested to determine whether the tissue sites adequately respond to the delivered pacing pulses. Once electrical testing is completed, the compact dual chamber intra-cardiac pacing device is considered fully deployed and the delivery device is removed from the heart.

One or more embodiments involve a lumenless T-shaped leadlet that is coupled to an atrial electrode. The T-shaped leadlet is configured to be pulled by a tether into a slotted tubular portion of the leadlet mover/torquer. The leadlet mover includes an open channel configured to receive the leadlet. The T-shaped leadlet folds back onto itself in a U-shape so that the leadlet does not interfere with LPD fixation of tines to tissue when the tines extend out of the delivery system device cup. The leadlet body makes a U-shape by folding back onto itself in the middle of the fork-shaped leadlet mover. The leadlet body folds back onto itself by a series of steps. For example, the leadlet mover/torquer is retracted into the device mover. The tether is pulled by the user, which in turn, pulls the leadlet into the device mover (i.e. coil) and folds the leadlet. The user continues pulling the tether so that the "T"-shaped end, located where the leadlet conductor turns 90 degrees, falls into a slot on the distal leadlet mover. The user continues pulling on the tether until the "T" in the lead conductor is seated at the proximal end of the slot.

One or more other embodiments relates to a hooped leadlet. The hooped leadlet includes a ring that surrounds the leadlet body at the distal end. A space exists between the inner surface of the ring and the outer surface of the leadlet body to allow a tether to pass therethrough. The tether is used in conjunction with the delivery device to control movement of the leadlet from a first position to a second position.

One or more embodiments are directed to a compact implantable medical device having leadlet fixation component (e.g. helix, tines etc.) and/or LPD fixation component (e.g. helix, tines etc.) that can be electrically active or not electrically active.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives. In the following, exemplary dimensions modified with "about" can be interpreted as being ±10% a designated value.

FIGS. 1-2 illustrate compact dual chamber intra-cardiac pacing device 8 that is configured to perform dual chamber intra-cardiac pacing. Compact dual chamber intra-cardiac pacing device 8 comprises a first implanted portion 88 in a right ventricle (RV) of a heart, in proximity to an apex, and a second implanted portion 86 in a right atrium (RA) of the heart, within or around atrial appendage 38. First implanted portion 88 can be leadlet pacing device (LPD) 10 that employs tines 12 to attach to ventricular tissue while second implanted portion 86 comprises leadlet 20 that attaches to atrial tissue through helical tip 21. Leadlet 20 connects first portion 88 to second portion 86. LPD 10 can generate different or the same pacing pulses to first and second portions 86, 88.

Figure 2A:
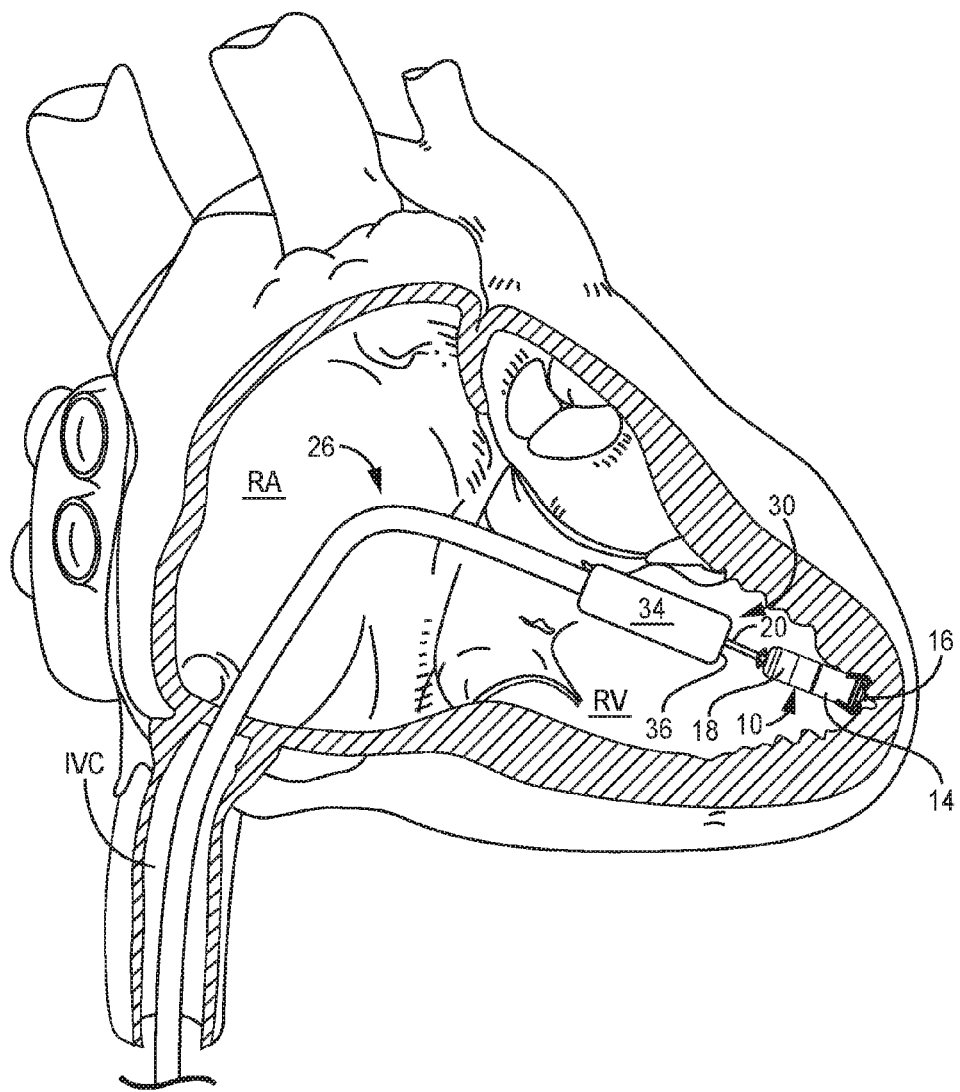
FIG. 2A is a schematic diagram of a delivery device advanced into a right ventricle for deployment of a ventricular portion of a compact dual chamber intra-cardiac pacing device.

FIG. 2A is a plan view of a relatively compact dual chamber intra-cardiac pacing device 8 implanted in a heart of a patient. The LPD 10, commercially available as MICRA™, a leadless pacing device manufactured by Medtronic, INC. located in Minneapolis, Minn., that can be employed for the present disclosure. LPD 10, hermetically sealed in housing 14, is configured to deliver pacing pulses through electrodes 16/18 and/or leadlet 20. An exemplary LPD 10 and tines 12, may be seen and described in greater detail with respect to U.S. Patent Pregrant Publication No. US-2012-0172690-A1, and Patent Application Ser. No. 62/281,312 filed Jan. 21, 2016, assigned to the assignee of the present invention, the disclosures of which are incorporated by reference in their entirety herein. LPD 10 is configured to pace cardiac tissue using different pacing modes such as DDD mode or VDD mode. DDD is part of the three-position NBG Pacemaker Code. The pacemaker device DDD code indicates that the implantable medical device provides dual chamber pacing, dual chamber sensing, and both triggered and inhibited modes of response (atrial triggered and ventricular inhibited). The DDD mode can be implemented by using the anode ring 180 and helical electrode 21 shown in FIG. 11. VDD mode indicates ventricular chamber pacing, dual chamber sensing, and both triggered and inhibited modes of response (atrial triggered and ventricular inhibited).

LPD 10 is preferably formed from a biocompatible and biostable metal such as titanium, which contains a pulse generator (e.g., a power source and an electronic controller—not shown), a plurality of fixation tines 12, collar 168, and electrodes 16, 18, for example, being coupled to the pulse generator by a conductor of an hermetic feedthrough assembly (not shown) that is constructed according to methods known to those skilled in the art of implantable medical devices. Delivery tool interface 88 and/or collar 168 are configured to be coupled by the delivery tool during retrival. Housing 14 may be overlaid with an insulative layer, for example, medical grade polyurethane, parylene, or silicone. Electrode 18, shown in FIG. 4A, may be formed by removing a portion of the insulative layer to expose the metallic surface of housing 14. According to the illustrated embodiment, electrode 16, shown in FIGS. 1-2, FIG. 4A and FIG. 6, and electrode 18 can be configured to perform bipolar pacing and/or sensing. Bipolar pacing involves optimal low thresholds to ensure long-term pace energy conduction and increased pacing device 10 longevity. Bipolar sensing electrodes can be tip-to-ring (i.e. helix 21 and ring 180 shown in FIGS. 11-12) that is selected to optimize detection of both R-waves and arrhythmias as well as rejection of t-waves.

A first embodiment leadlet 20, referred to as the T-shaped leadlet, is shown in FIG. 2C and FIGS. 4-7. Leadlet 20 comprises a body 23, eyelet tether 52, junction 158, the helix 21, a T-shaped distal end 76, and a leadlet guide 170, each of which is described below.

Figure 6:
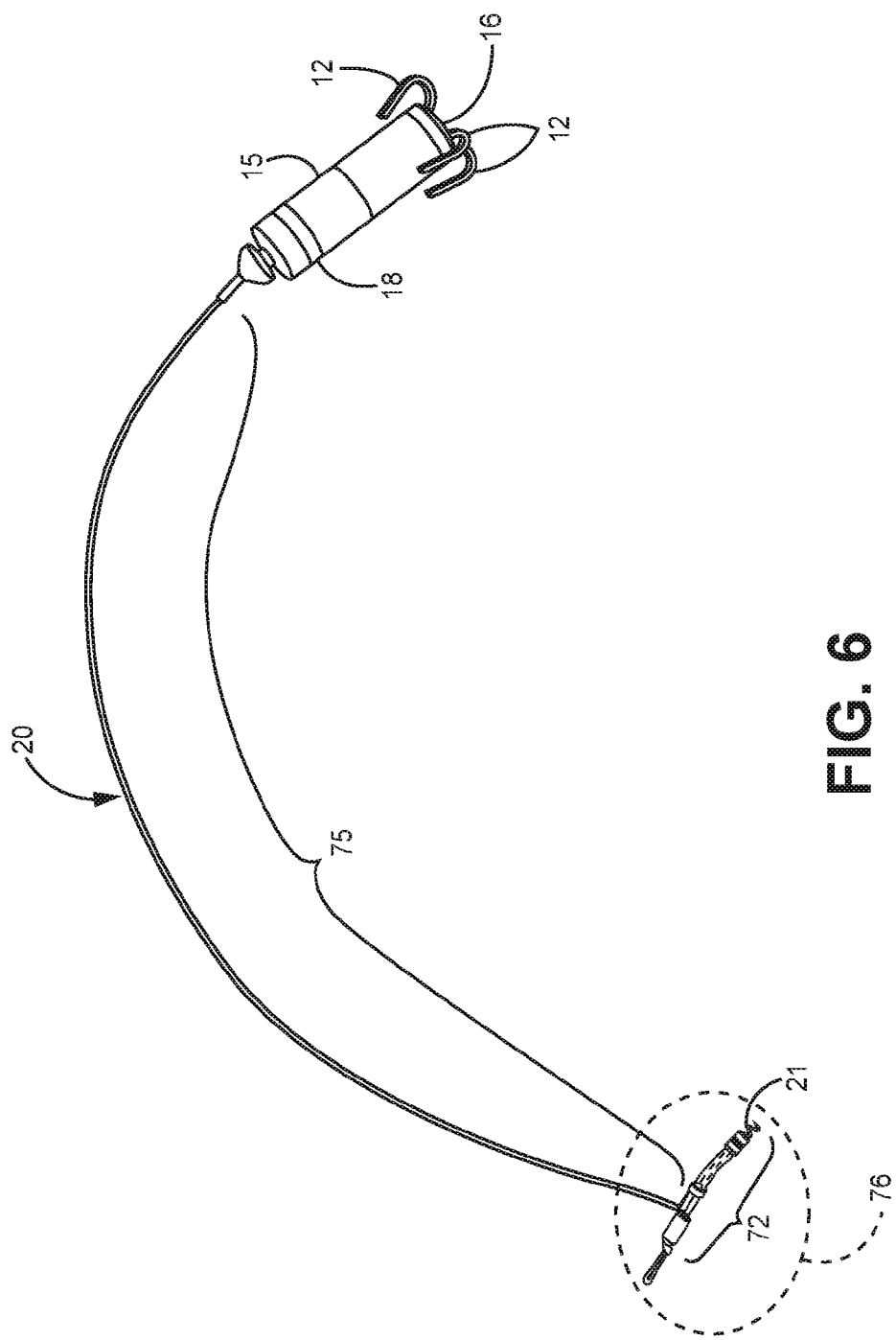
FIG. 6 is a perspective view of a T-shaped leadlet coupled to a pacing device.

The leadlet body 23 is shown to extend the length of leadlet 20 in FIG. 6 and then breaks away from short bar 72 (i.e. about 90 degrees away from the length of the leadlet 20). The body 23 can comprise a single electrical conductor 19 (FIG. 2C also referred to as a cable), without a lumen, that connects with helix 21 for delivery of electrical stimulation. Medtronic model SELECTSURE™ 3830 manual (2013), incorporated herein by reference in its entirety, shows and describes an exemplary lead body 23 that can be employed for leadlet 20. Two or more conductors with or without lumens can also be used to form a leadlet of the present disclosure. An elongated conductor 19 of leadlet 20, which extends through another hermetic feedthrough assembly (not shown), and within an insulative tubular member of leadlet 20 (FIG. 6), electrically couples the aforementioned pulse generator (contained within housing 14) to the helix 21. The conductor may be formed by one or more electrically conductive wires, for example, MP35N alloy known to those skilled in the art, in a coiled or cabled configuration, and insulative tubular member may be any suitable medical grade polymer, for example, polyurethane, silicone rubber, or a blend thereof. According to an exemplary embodiment, flexible leadlet body 20, extends a pre-specified length (e.g. 10 cm to 20 cm, or 15 cm to 20 cm) from a proximal end of housing 14 to the other end. The leadlet body is less than 7 French (Fr) but typically in the range of 3 to 4 FR in size. In one or more embodiments, 2 to 3 FR size leadlet body is employed.

Eyelet tether 52, coupled to tether 50, are pre-loaded onto leadlet 20, as shown in FIGS. 3A-3C FIGS. 6-7, FIGS. 9A-9B and FIG. 12. Eyelet tether 52, coupled to tether 50 allow the leadlet 20 to be moved from one tissue site to another tissue site. Once the leadlet 20 has been implanted, the physician can cut one of the legs of tether 50 and pulls it out to remove.

Figure 5:
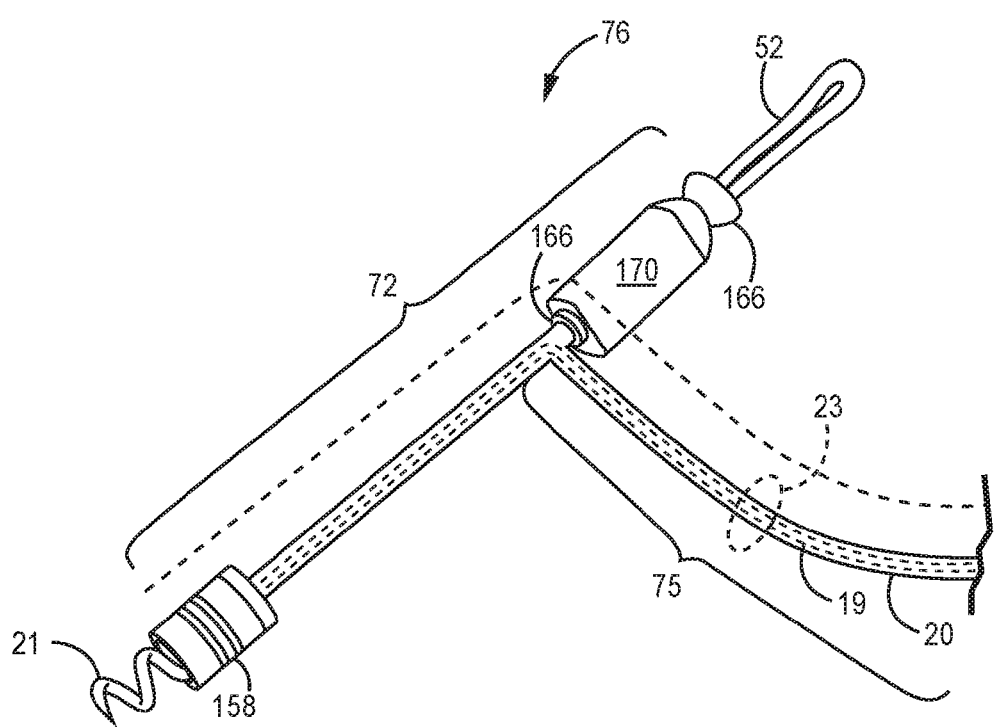
FIG. 5 is a perspective view of a distal end of the T-shaped leadlet.

Junction 158, shown in FIG. 5, ensures that the helix 21 is securely and stably attached to the conductor. Junction 158 is located between the helix 21 and conductor of the leadlet 20. Junction 158 includes a lumen (not shown) for receiving the leadlet 20 to attach to helix 21, which can serve as an electrode for sensing and/or pacing.

Leadlet 20 comprises a T-shaped distal end 76 as shown in FIG. 5 that allows the user to spin or turn leadlet through the leadlet mover 60 configured as a slotted tube and described in greater detail below relative to FIG. 8. T-shaped distal end 76 comprises short bar 72 and an elongated portion 75. The short bar 72 (FIG. 5) includes the tether 52 to allow the tether 52 to be anchored in or near the junction 158 and generally minimize forces on the lead body 23 at the tether attachment point. It is used during moving of leadlet 20 into, for example, a lumen of the leadlet mover 60 to position the leadlet 20 near cardiac tissue.

Figure 3A:
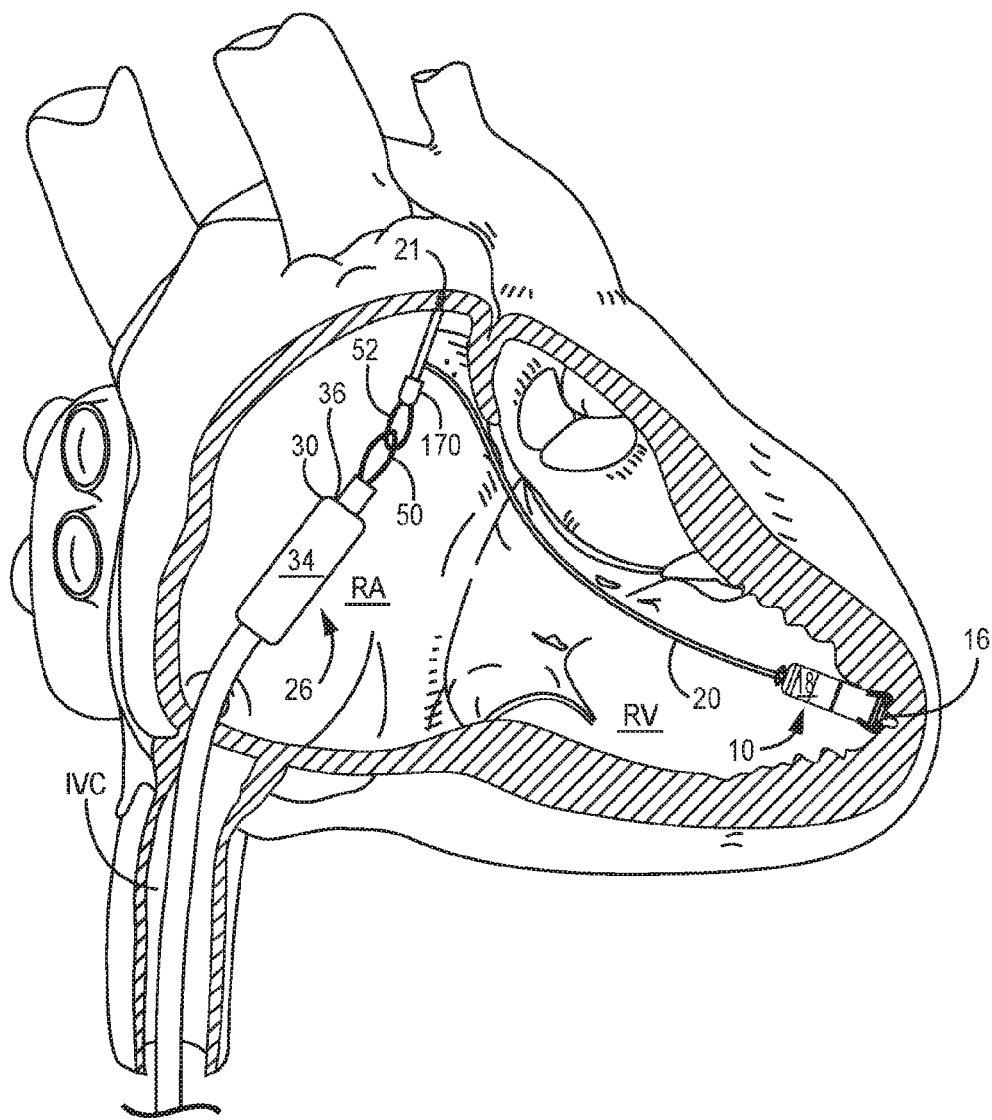
FIG. 3A is a schematic diagram related to an acute retrieval in which a snare is attached to a collar of the pacing device.
Figure 3B:
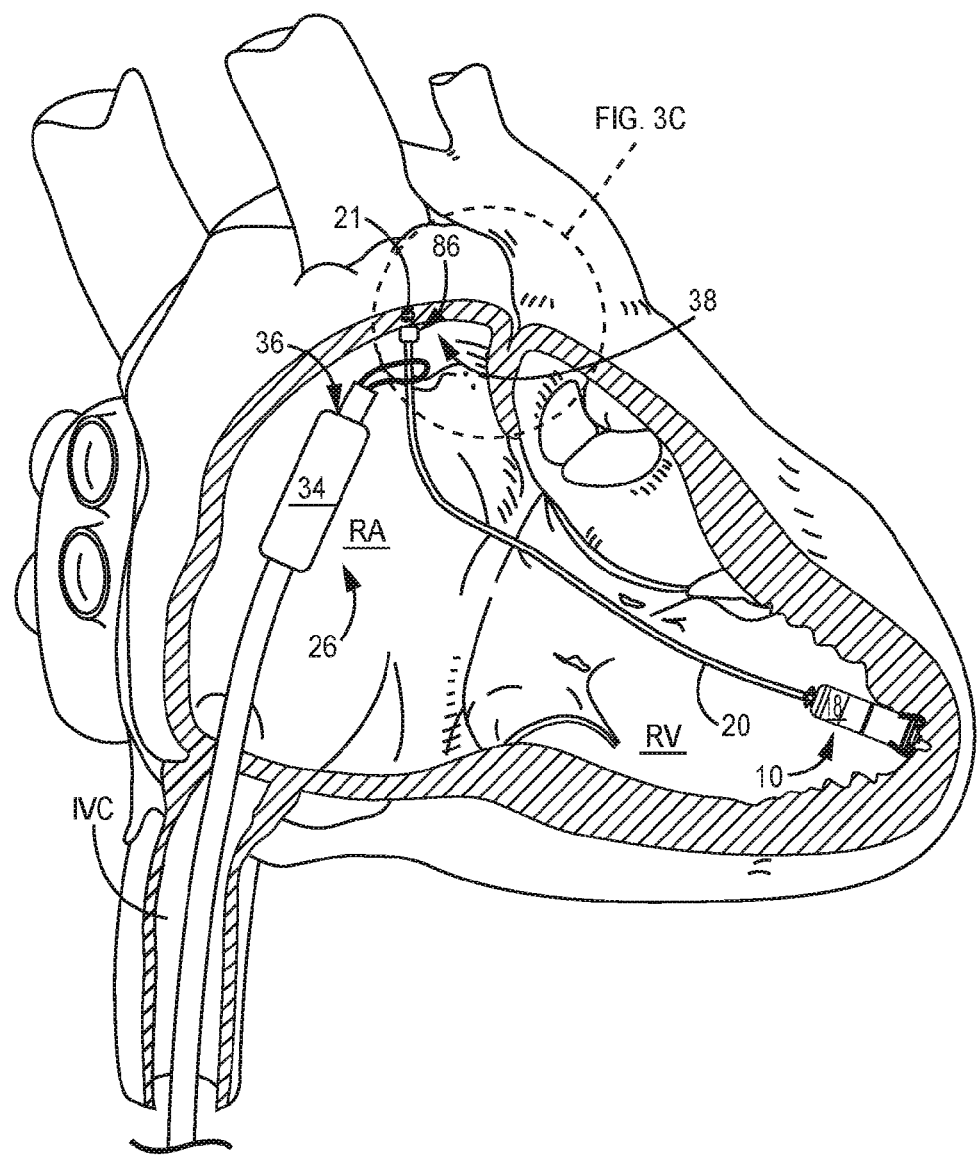
FIG. 3B is a schematic diagram related to another acute retrieval method for removing the pacing device.
Figure 3C:
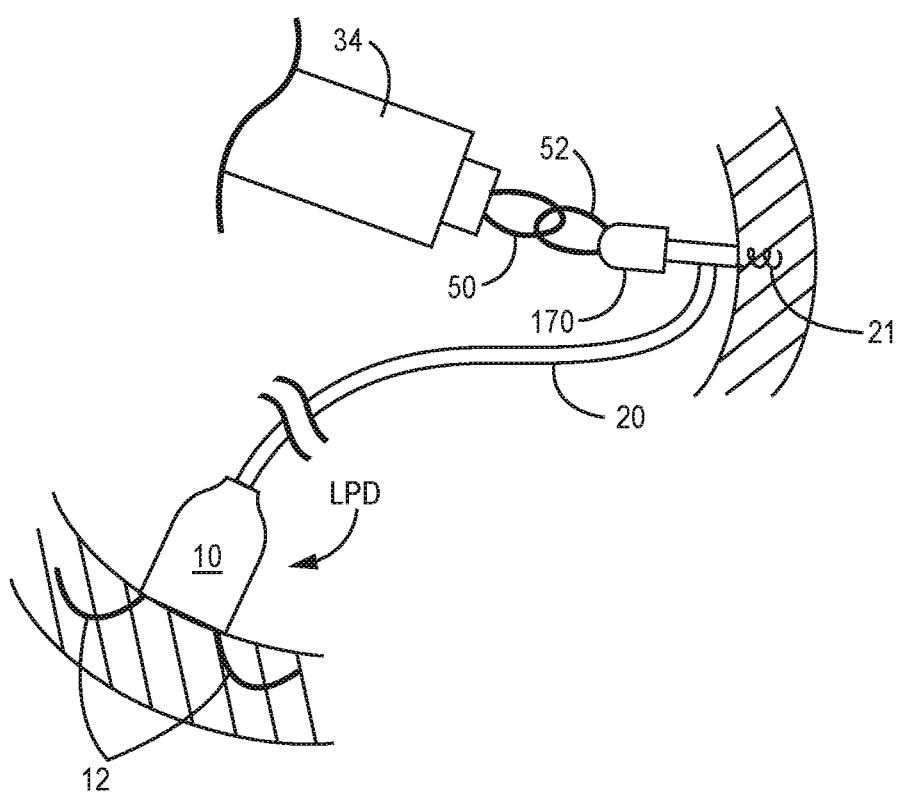
FIG. 3C depicts a pacing device with a first leadlet embodiment according to FIG. 3A, referred to as T-shaped leadlet, is fixated in the heart.
Figure 7:
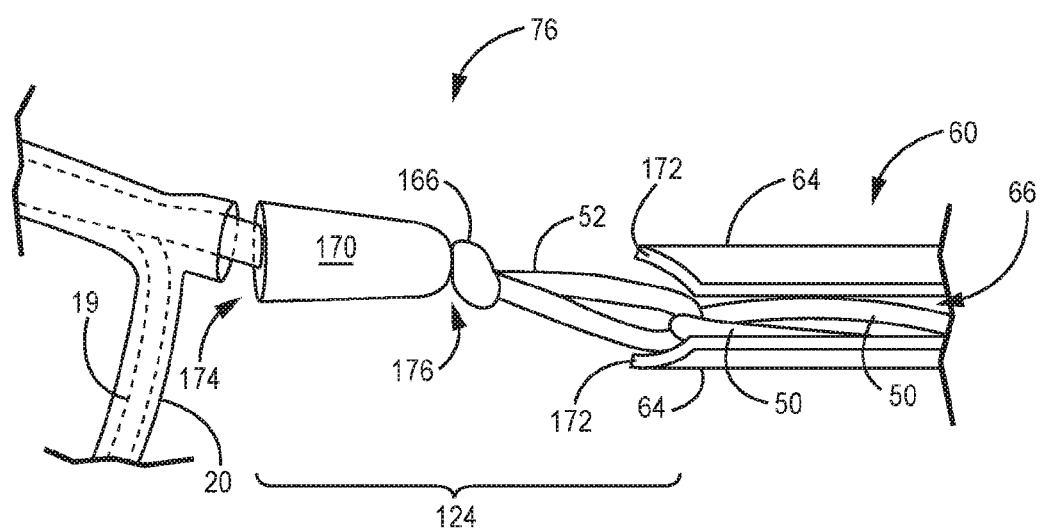
FIG. 7 is a perspective view of a T-shaped leadlet and leadlet guide being moved into a leadlet mover.

As shown in FIGS. 5 and 7, leadlet guide 170 is used as a "bumper" to position and/or prevent damage from occurring to the leadlet 20 as leadlet 20 is moved into a distal end 61 of the leadlet mover 60. By moving leadlet 20 into the leadlet mover 60 (FIG. 8), leadlet 20 can be moved from one tissue site that may not be electrically responsive to delivered electrical paces to another tissue site that achieves improved responsiveness to attach the leadlet 20. Leadlet 20 is removed from one tissue location by unscrewing helix 21 from the tissue by leadlet 20, disposed in one of the slots 66 of the leadlet mover 60. By leadlet being located in one of the slots 66, the leadlet mover 60 can be positioned to torque leadlet 20 in order to rotate (e.g. screw-in or unscrew) the helix 21 from tissue by using an exemplary tether/snare configuration (FIGS. 3A-3C). The tether/snare configuration can be used to tightly grab the leadlet body 23 to control (rotate/extend) and fixate the leadlet. Leadlet retrieval generally involves reversing the steps relative to FIGS. 11-12. Leadlet guide 170 is gum-dropped shaped in which one end 174 has a larger diameter (e.g. 1.65 mm (0.65 in), 0.051 in or other suitable dimensions) compared to a smaller diameter (e.g. 1.25 mm) on the other end 176 as shown in FIG. 7. The rounded, smaller diameter end 176 passes or enters between the inner surfaces of the forks 64 of leadlet mover 60 before the larger diameter end 174 passes between the inner surfaces of the forks 64. By pulling the smaller diameter end 176 passes or enters between the inner surfaces of the forks 64 of leadlet mover 60 before the larger diameter end 174, the leadlet guide 170 positions the leadlet 20 into the leadlet mover 60 thereby reducing the chances of the leadlet 20 being damaged. The diameter between the inner surface of the forks 64 is about 1.83 mm. By having the smaller diameter end 176 enter the forks 64 of leadlet mover 60, leadlet guide 170 gradually centers and guides the leadlet 20 into the leadlet mover 60. Optionally, tether knot 166 provides support and tightness to tether 52.

Figure 2B:
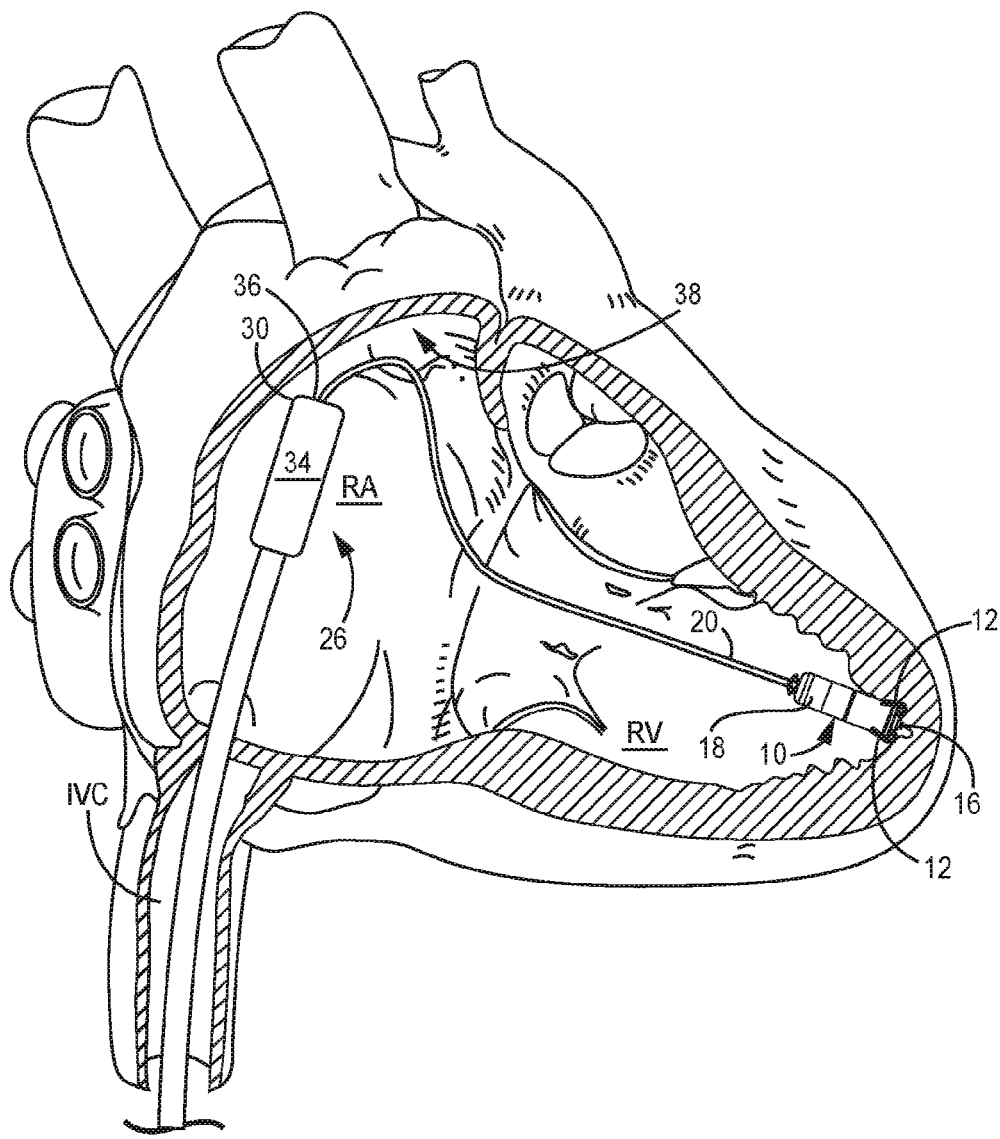
FIG. 2B is a schematic diagram of a delivery device positioned in a right atrium for deployment of the atrial portion of the device.
Figure 2C:
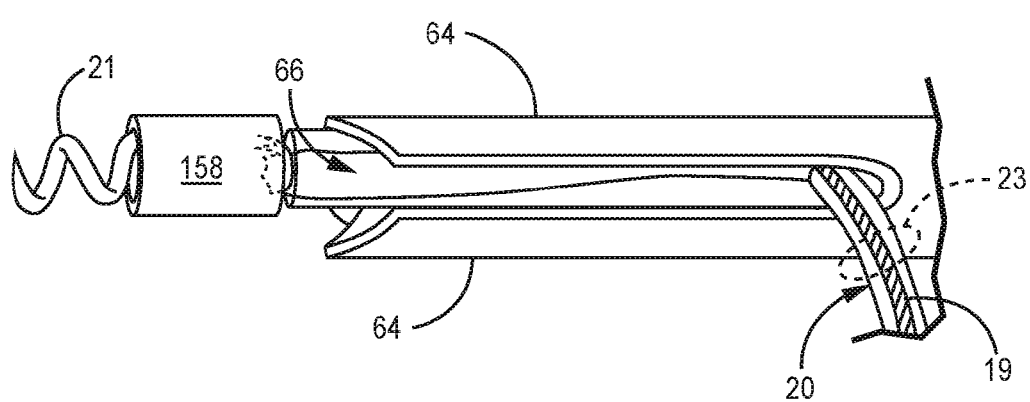
FIG. 2C is an enlarged perspective view of a leadlet mover that is configured to push, move and/or torque a leadlet into tissue.

Leadlet mover 60, shaped like a tuning fork or slotted tube, comprises forks 64 or prongs, base 67, and coil 62. Forks 64 or prongs of the leadlet mover 60, located at the distal end 61 of the leadlet mover 60, extend from base 67 and coil 62, as shown in FIG. 2C and FIGS. 7-8. Leadlet mover 60 is preferably formed from a single piece but can be formed from multiple pieces of material (e.g. stainless steel). Leadlet mover 60 comprises and elongated tubular element formed by forks 64, coil 62 and substantially straight wire 65. First and second slots 66, formed by first and second prongs associated with the leadlet mover 60, are diametrically opposed from each other. Forks 64 are welded or crimped onto a coil 62. The coil 62 has a length (e.g. 20-22 cm) that forms into a straight or substantially straight wire 65 and exits through proximal port 94b. The distal end of leadlet mover is hollow (e.g. 4 inches from the distal end) and is solid from the coil to proximal end of leadlet mover 60. The leadlet 20 is guided into the tapered 172 (optional) of prongs 64 when the user pulls on a tether to reload the leadlet 20 into leadlet mover 60. Once the leadlet 20 snaps into position by contacting proximal end 71 of slot 66 located near proximal end 69 of the prong pocket shown in FIG. 8, the leadlet 20 is considered loaded into the leadlet mover 60 and can be moved to another tissue site.

After the ventricular portion 88 of the compact device 8 is deployed out through a distal opening 36 of a delivery device 26 (also referred to as a delivery tool), the atrial portion 86 is deployed. FIG. 1, FIG. 2A and FIG. 2B show atrial portion 86 of compact dual chamber intra-cardiac pacing device 8 implanted in RA, according to one or more embodiments. A portion of the right atrial wall, for example, in appendage 38 (FIG. 1), has a laminate structure that includes an inner layer of pectinate muscle (PM) and an outer layer of visceral pericardium (VP), which forms the epicardial surface. Atrial portion 86 is secured at the implant site by fixation means 21 (e.g. helix, tines etc.) penetrating through the layer of PM without perforating through the VP and causing pericardial effusion. According to one or more embodiments, the leadlet 20 unfolds when the leadlet mover/torquer 60 is extended beyond the device mover 39 formed by intermediate member 32 and coiled distal end 43 shown in FIG. 4A and FIG. 8.

Skilled artisans understand that device mover 39 can be preferably configured such that outer member 34 retracts thereby causing LPD 10 to exit delivery device 26. Suitable construction detail for such an exemplary delivery device 26 is described in commonly assigned U.S. Pat. No. 9,526,522 issued Dec. 27, 2016, the description of which is hereby incorporated by reference in its entirety. Another exemplary device mover 39 can be configured such that outer member 34 can be configured to push at the proximal end 45 of LPD 10 described in U.S. Pat. No. 9,414,857 B2 issued Aug. 16, 2016, the description of which is hereby incorporated by reference in its entirety. Either way for delivering the LPD 10 can be employed by the present disclosure.

Figure 14:
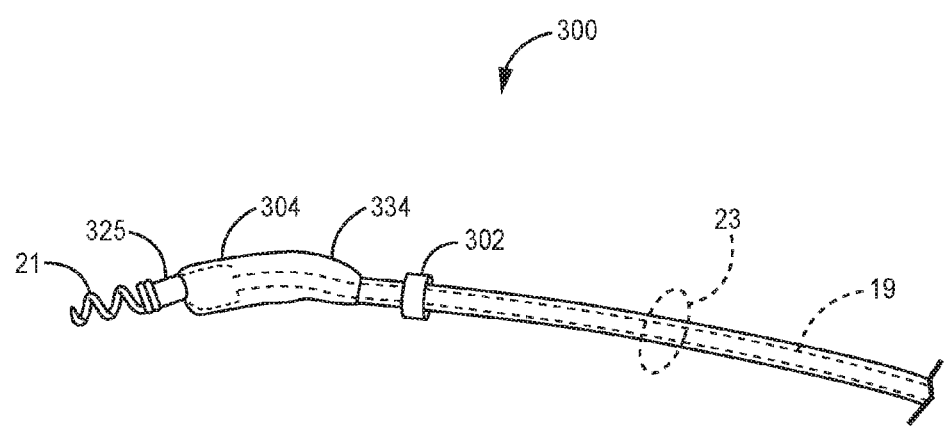
FIG. 14 is an enlarged schematic view of the second leadlet embodiment shown in FIG. 13 in which a ring is used in combination with a tether to pull the leadlet into the lumen of the delivery device.
Figure 15:
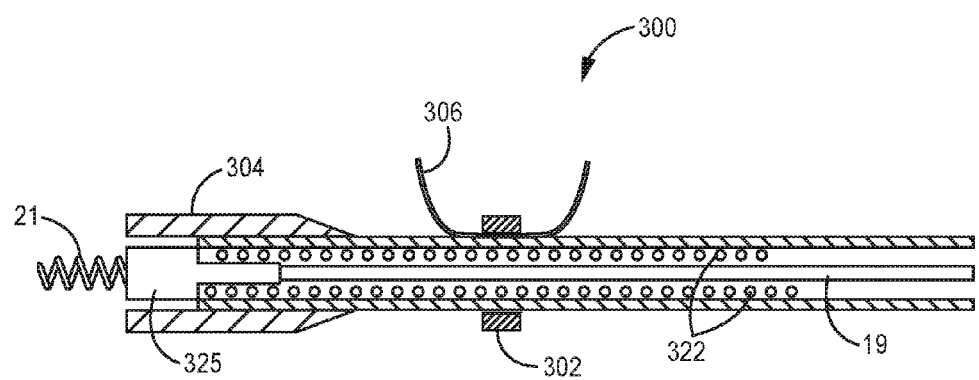
FIG. 15 is a cross-sectional distal end view of the second leadlet embodiment shown in FIG. 14 in which a ring is used in combination with a tether to pull the leadlet into the lumen of the delivery device.
Figure 16A:
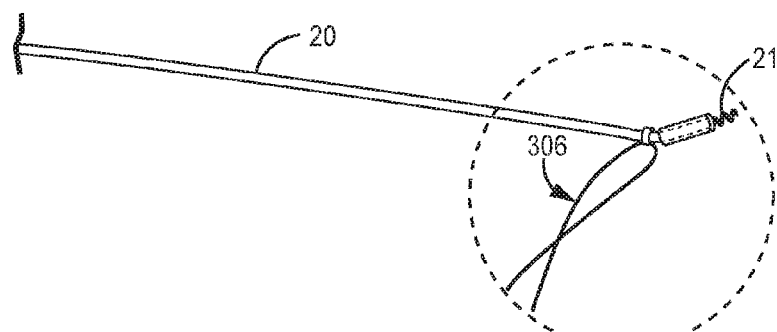
FIG. 16A depicts a schematic view of the second leadlet embodiment depicted in FIG. 15 in which a tether is inserted through the leadlet ring to form a hoop.
Figure 16B:
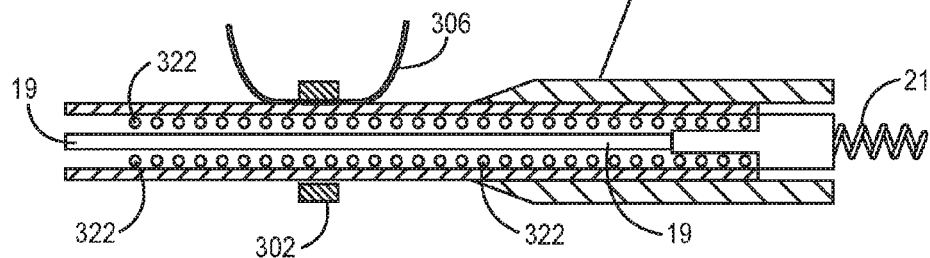
FIG. 16B depicts an enlarged cross-sectional longitudinal view of the second leadlet embodiment shown in FIG. 16A.
Figure 17A:
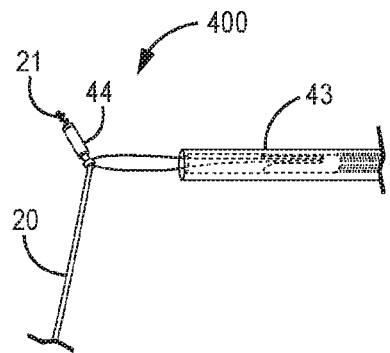
FIG. 17A depicts a schematic view of the second leadlet embodiment, shown in FIG. 16, in which the leadlet is being re-loaded into the delivery device in order to reposition the leadlet from one tissue site to another tissue site to determine optimal tissue location.
Figure 17B:
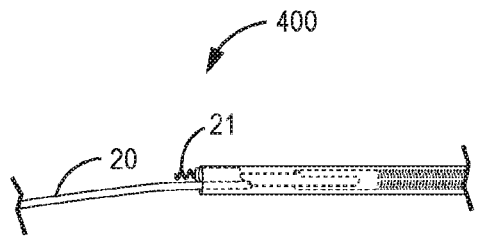
FIG. 17B depicts a schematic view of the second leadlet embodiment, shown in FIG. 17A, in which the helix is exposed but the remaining portion of the leadlet is substantially loaded into the device mover
Figure 17C:
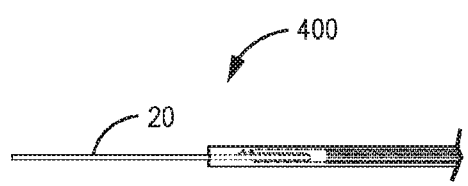
FIG. 17C depicts a schematic view of the second leadlet embodiment, shown in FIG. 17B, in which the leadlet is completely loaded into the lumen of the delivery device.
Figure 17D:
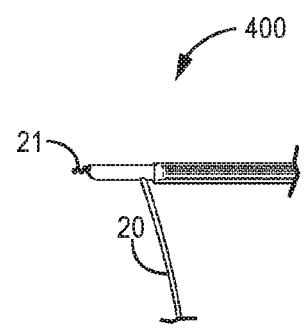
FIG. 17D depicts a schematic view of the second leadlet embodiment, shown in FIG. 17C, in which the leadlet has been moved to another tissue location and the leadlet mover has been used to reposition the leadlet out of the distal end of the delivery device.
Figure 17E:
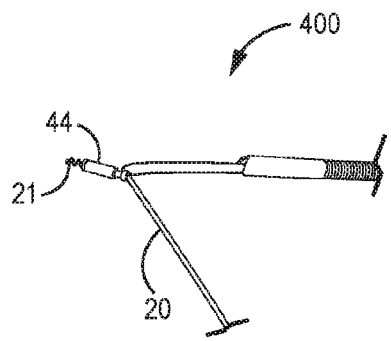
FIG. 17E depicts a schematic view of the second leadlet embodiment in which the leadlet has exited the distal end of the delivery device and is ready to be counter-rotated around the leadlet mover in order to create sufficient stress in the leadlet body to attach the helix to tissue during rotation of the leadlet.
Figure 18A:
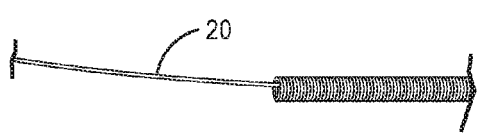
FIG. 18A depicts a schematic view of a leadlet helix that is substantially hidden within the lumen of the distal end of the delivery device.
Figure 18B:
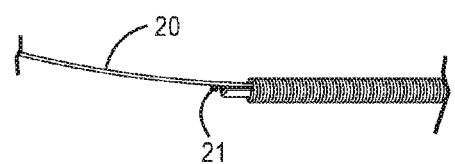
FIG. 18B depicts a schematic view of the leadlet helix is starting to exit the distal end of the delivery device.
Figure 18C:
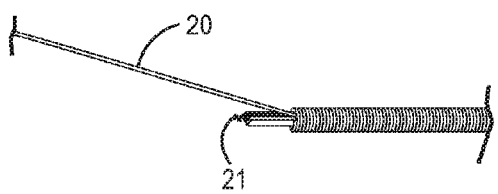
FIG. 18C depicts a schematic view of the leadlet helix extending further outside of the distal end of the delivery device.
Figure 18D:
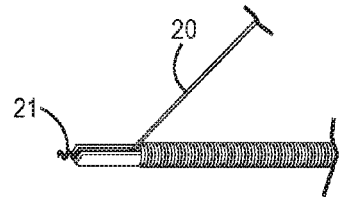
FIG. 18D depicts a schematic view of the leadlet as having transferred torque using the leadlet mover.

The helical tip 21 is configured to have a certain pitch that penetrates the PM without perforating the VP. Preferably, helix 21 comprises a right handed pitch, shown in FIG. 14. Other exemplary helix 21 that may be used is disclosed in U.S. Pat. No. 8,755,909 B2 issued Jan. 17, 2014, and assigned to the assignee of the present invention, the disclosure of which is incorporated by reference in its entirety herein.

Referring to FIGS. 3-7, FIG. 9 and FIG. 11, delivery device 26 is shown and described in greater detail relative to the steps of implanting the atrial portion 86 of device 8, which is after the user has deployed ventricular portion 88 of the device 8 in the RV. Delivery device 26 comprises proximal end 31, distal end 30 with a lumen 47 therethrough, as shown in FIG. 4A. Delivery device 26 functionally includes a device mover 39 (shown in FIG. 4A), a leadlet mover 60/65 and handle 58 shown in FIGS. 9A-9B.

Figure 4A:
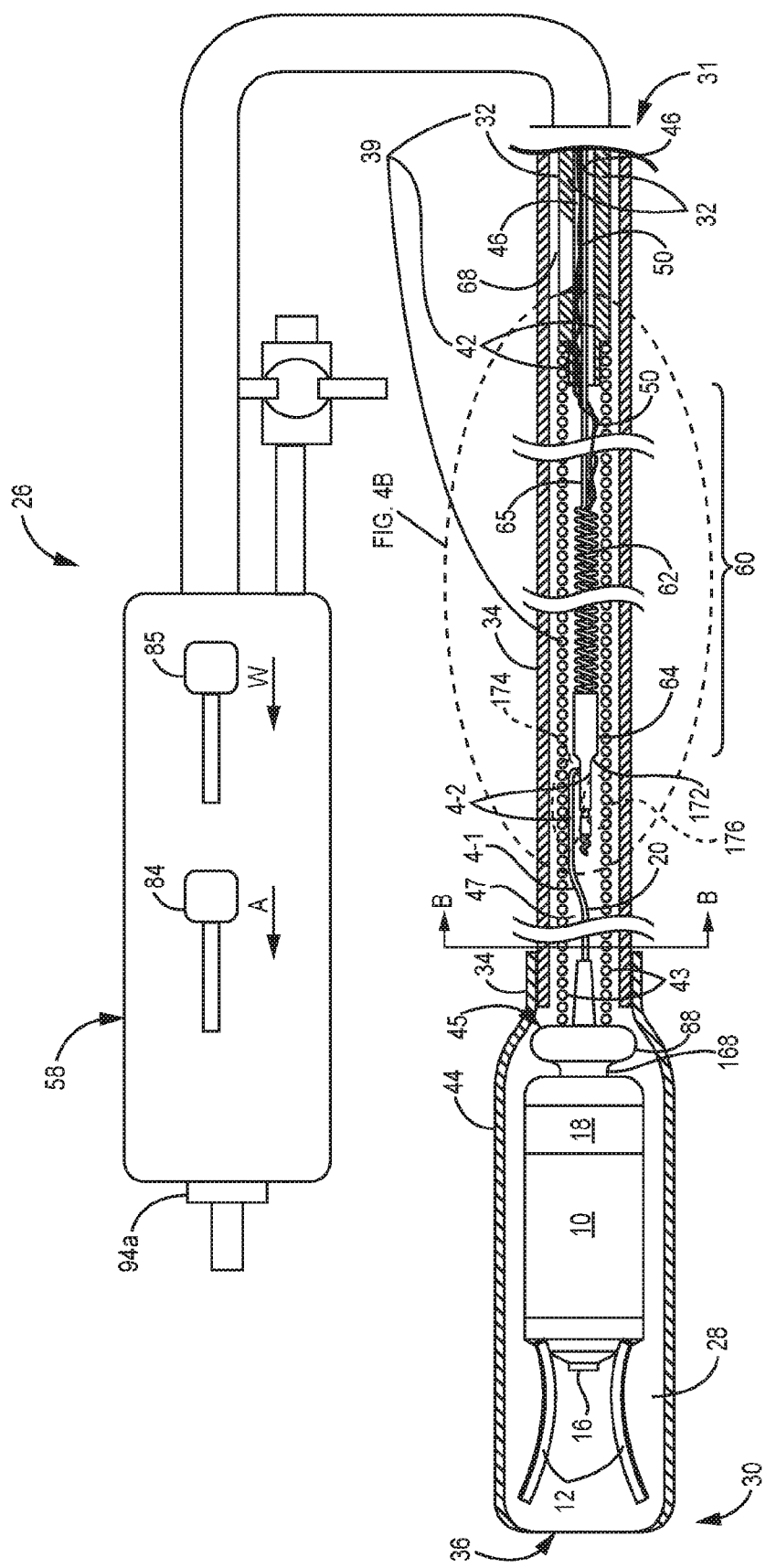
FIG. 4A is a longitudinal cut-away section plan view of a compact dual chamber implantable medical device residing in a lumen of a delivery device.
Figure 4B:
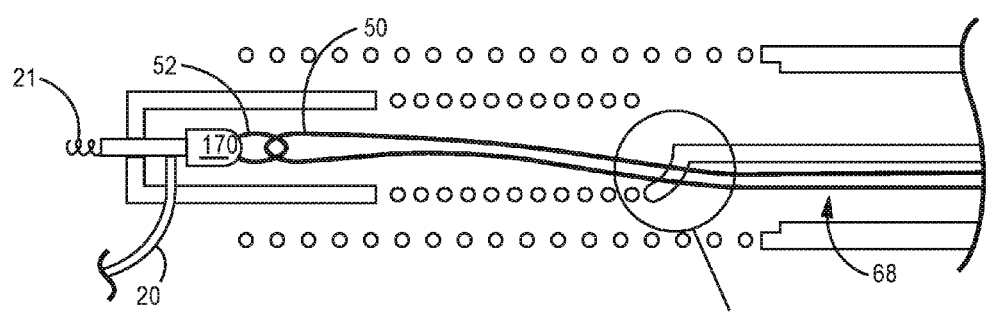
FIG. 4B is a plan view of a portion of the delivery device depicted in FIG. 4A.
Figure 4C:
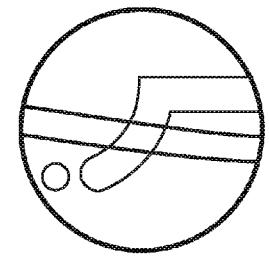

Device mover 39 comprises intermediate member 32 and a coiled distal end 43. Conceptually, the outer member 34, intermediate member 32, and leadlet mover 60/65 are similar to three stacked tubes, as is shown in FIG. 4, FIG. 8 and FIGS. 11-12. As previously stated, device mover 39 can be configured so that retracting outer member 34 causes LPD 10 to exit out of the distal end 30 of the delivery device 26 in response to the user engaging button 85 as is shown in FIG. 4A. Button 84 causes deflection and curve in FIG. 9.

Outer member 34 defines an outer shaft or tube of the delivery device 26 and holds intermediate member 32. Outer member 34 is an outer tube extending from the proximal end at handle 58 to the distal tip and forms a lumen (not shown) in which intermediate member 32 resides.

Intermediate member 32 of device mover 39 is configured to hold leadlet mover 60 in position. Intermediate member 32 comprises a coiled distal end 43 shown in FIG. 4A and a shaft 32. Intermediate member 32 extends from the handle 58 to the coiled distal end 43 and forms a lumen 47 to support LPD 10 and contain leadlet 20 during delivery of LPD 10 and leadlet 20 to ventricular and atrial tissues.

Intermediate member 32 can also include a pull wire assembly (not shown) integrated therein. The pull wire assembly may be coupled to a control member similar 84 and/or 85 of handle 58 that causes intermediate member 32 to bend along distal portions thereof. A length of outer member 34, between handle 58 and distal opening 36, when outer member 34 is in the position shown in FIG. 4A, may be about 110 cm, for example, to reach into the right ventricle (RV) from the femoral access site.

Prior to loading compact device 8 into delivery device 26, atrial portion 86 is reoriented relative to ventricular portion 88 by bending and/or folding leadlet 20 as shown in FIG. 4A. To load device 8 into delivery device 26, the user may employ a tether 50 of delivery device 26 (FIG. 4B) engaged to tether 52 at a zone 124 (FIG. 7) that coincides with folding first and second segments 4-1 and 4-2 shown relative to FIG. 4A. According to the illustrated embodiment, opposing lengths of tether 50 extend within lumen 46 of intermediate member 32 so that tether 50 loops around leadlet 20 for engagement therewith, and proximal ends 50 of the tether lengths protrude from a proximal port opening 94b (FIG. 9A) of delivery tool 26, where an user may grasp them. The user may pull proximal ends of tether 50, to draw folded segment 4-2 of leadlet 20 in through a distal opening of lumen 28, followed by atrial portion 86, and then followed by ventricular portion 88. Ventricular portion 88 is loaded last into device 26 so that ventricular portion 88 can be first delivered to ventricular tissue followed by delivery of the atrial portion 86.

Figure 20:
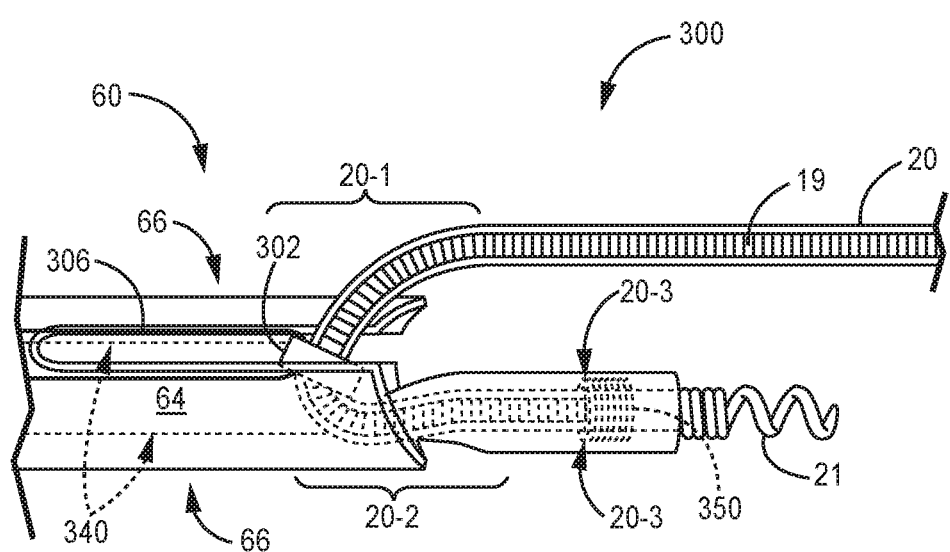
FIG. 20 depicts a schematic view of the second leadlet embodiment of FIG. 19 in which the leadlet is folded onto itself in a U-shape while disposed in a lumen of the lead let mover.

The T-shaped leadlet 20 folds back onto itself in a U-shape configuration partially shown in FIG. 4A. The U-shape configuration of the leadlet 20 does not interfere with LPD 10 fixation of tines 12 to tissue when the tines 12 extend out of the delivery system device cup 44 or tubular sidewall that holds LPD 10 in position. Device cup 44 defines a distal portion of outer member lumen 28. FIG. 20 shows the U-shape configuration more clearly with respect to the hooped leadlet 300 embodiment but skilled artisans should be able to appreciate that the same or similar U-shape configuration will apply to the T-shaped leadlet embodiment. Referring back to FIG. 4A, the leadlet body 23 makes a U-shape configuration by folding a first segment 4-1 back onto itself of second segment 4-2 in the middle of the fork 64 shaped leadlet mover 60. The leadlet body 23 folds back onto itself by a series of steps. For example, the leadlet mover and/or torquer 60 is retracted into the device mover 39 shown in FIG. 4A. The tether 50 is pulled by the user, which in turn, pulls the leadlet 20 into the device mover (i.e. coil) and folds the leadlet 20. The user continues pulling the tether 50 so that the "T"-shaped distal end 76, located where the lead conductor turns 90 degrees shown in FIG. 5, falls into a slot 66 (FIGS. 8A-8B) on the distal end 61 of the leadlet mover 60. The user continues pulling until the "T" in the lead conductor is seated at the proximal end 69 of the slot 66 shown in FIG. 8A.

Figure 8A:
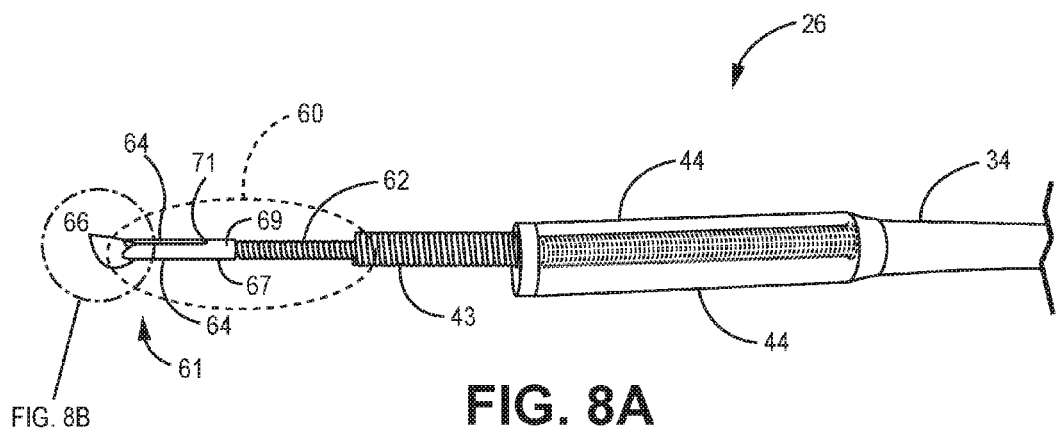
FIG. 8A is a perspective view of a distal end of the leadlet mover.
Figure 8B:
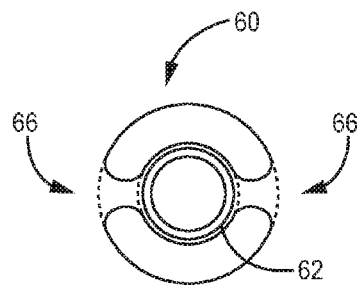
FIG. 8B is a cross-sectional view of the leadlet mover distal end shown in FIG. 8A that shows the slots formed by the forks extending from a base of the leadlet mover.
Figure 8C:
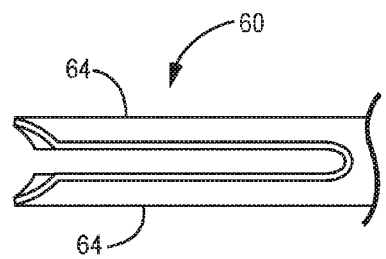
FIG. 8C is a side view of the leadlet mover prongs shown in FIG. 8A.

Referring to FIG. 2C and FIGS. 7-8, a leadlet mover 60/65 is preferably formed from a single piece but can be formed from multiple pieces of material (e.g. stainless steel). Leadlet mover 60 comprises tubular-like element formed by forks 64, coil 65 and substantially straight wire 65. Forks 64 are shaped like a tuning fork 63 with first and second prongs 64 extending from a base 67. First and second slots 66, formed by first and second forks 64 or prongs associated with the leadlet mover 60, are diametrically opposed (FIG. 8B) from each other. Forks 64 are welded or crimped onto a coil 62 shown in FIG. 8A. The coil 62 has a length (e.g. 20-22 cm) that forms into a straight or substantially straight wire 65 and exits through proximal port 94b.

Figure 9A:
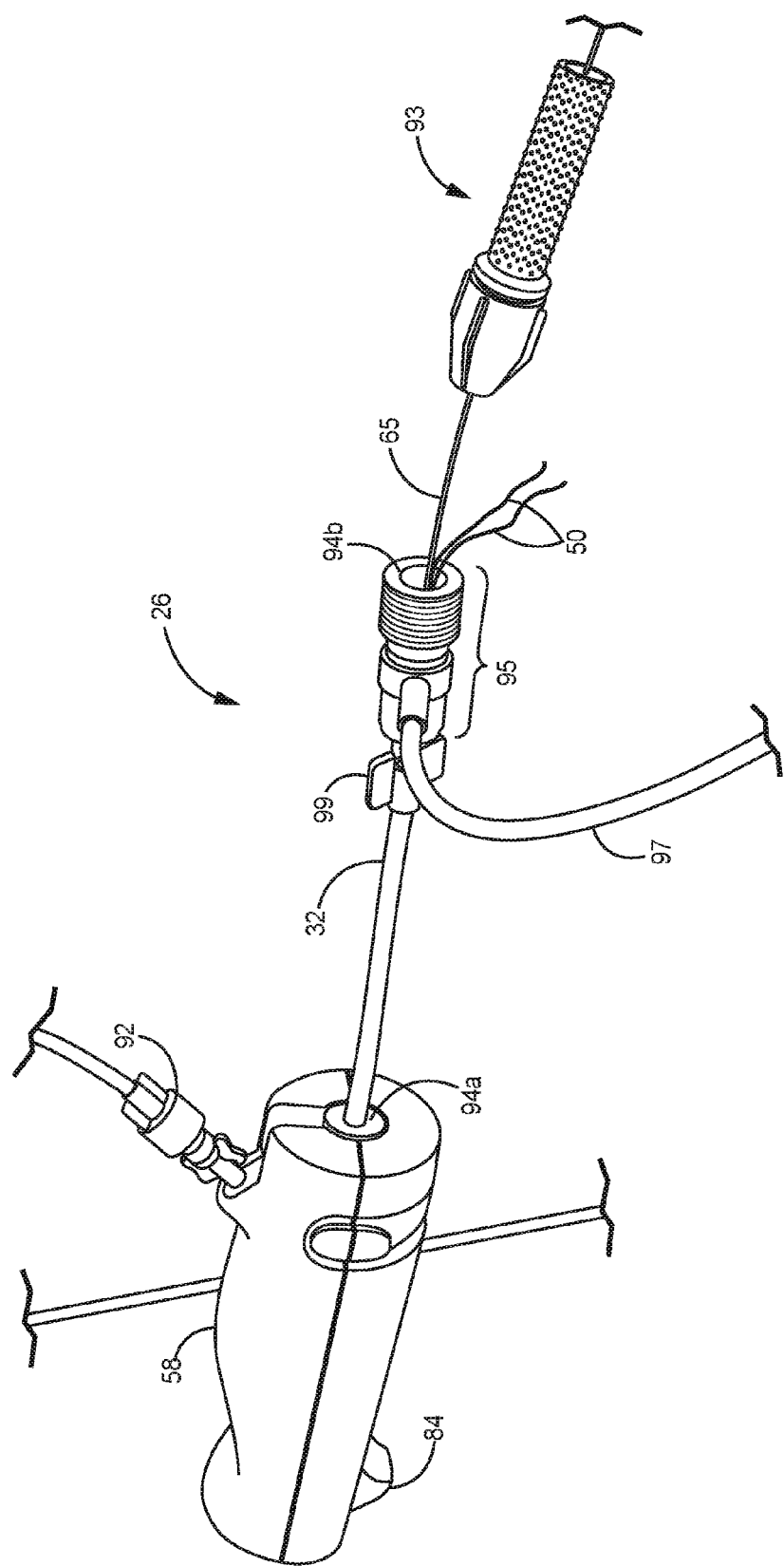
FIG. 9A a perspective view of a delivery device for a dual chamber intra-cardiac pacing device in which tethers for controlling delivery of the device exit a Tuohy-Borst valve.
Figure 9B:
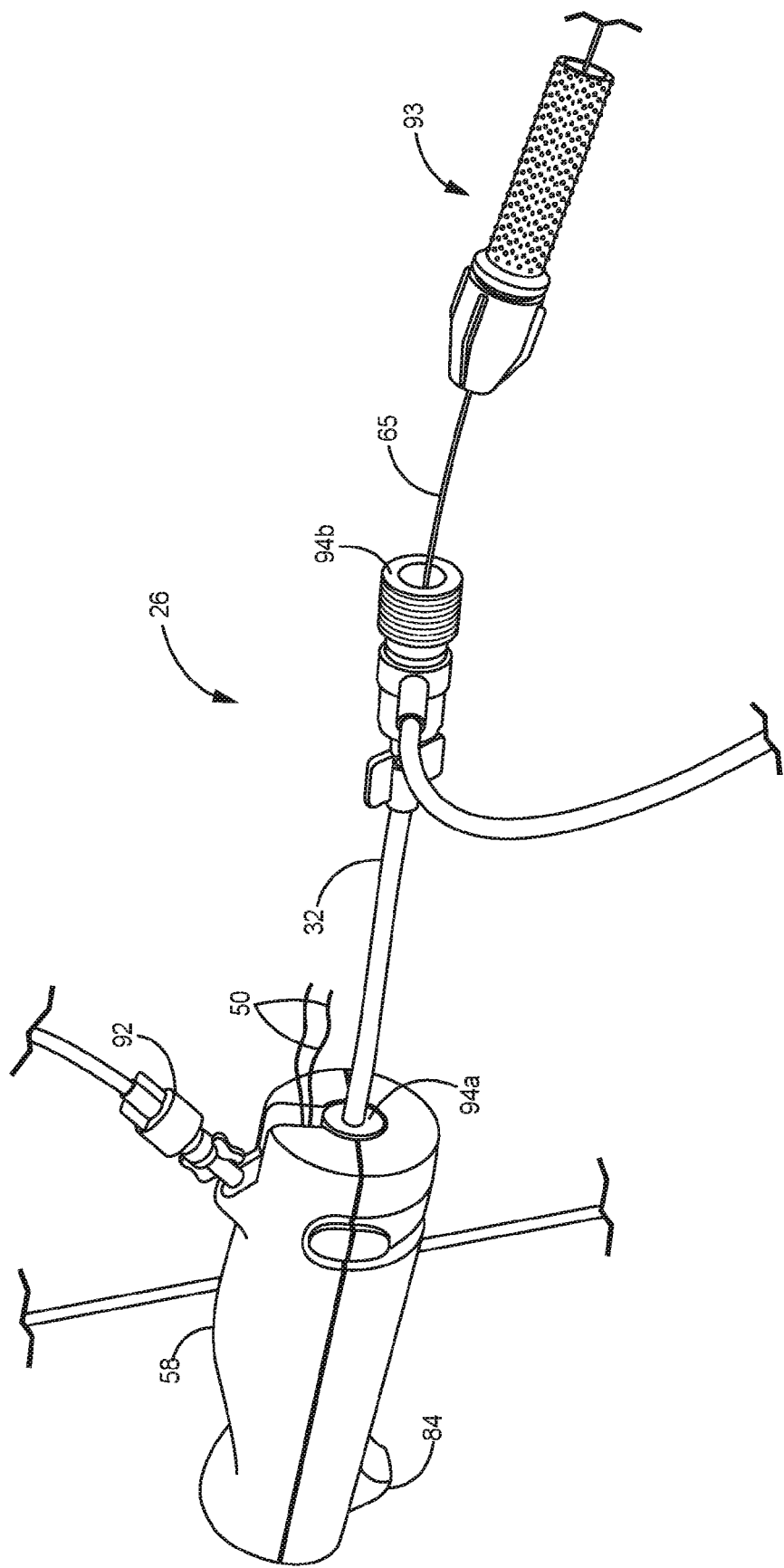
FIG. 9B is a perspective view of a delivery device for a dual chamber intra-cardiac pacing device in which tethers for controlling delivery of the device exits a handle.

A loop can be formed from tether 50, as is shown in FIG. 7 in order to attach to eyelet 52 to pull leadlet 20. The tether 50, shown in FIG. 4, extends through a lumen or opening between the forks 64 out of the coil 62. The tether then travels all the way through the device mover 39 and exits from port 94b, as shown in FIG. 9A. In an alternate embodiment, the tether 50 exits delivery tool 26 through port 94a as shown in FIG. 9B. Here, the tether takes a path through a side port 68 in the device mover and runs alongside the inside of the deflectable outer shaft before exiting the delivery tool.

The eyelet tether 52 is located along the distal end 76 of the leadlet, which runs along a portion of the T-shape distal end 76 (FIGS. 5-6).

Figure 10:
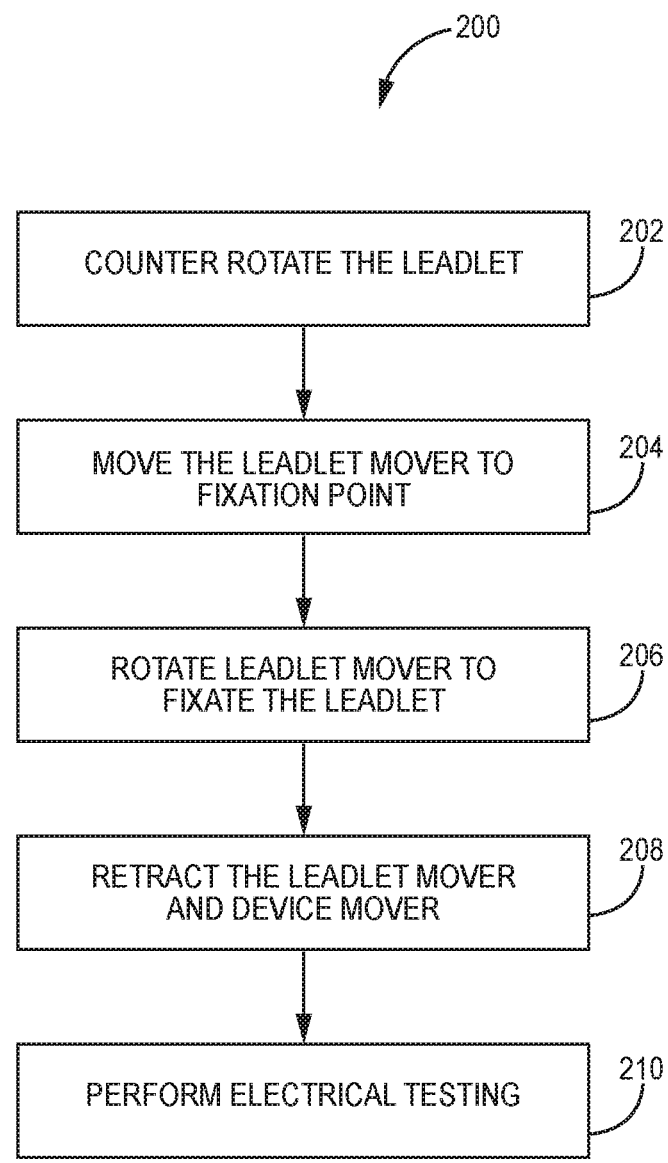
FIG. 10 is a flow diagram for securing a pacing device leadlet to atrial tissue.
Figure 11:
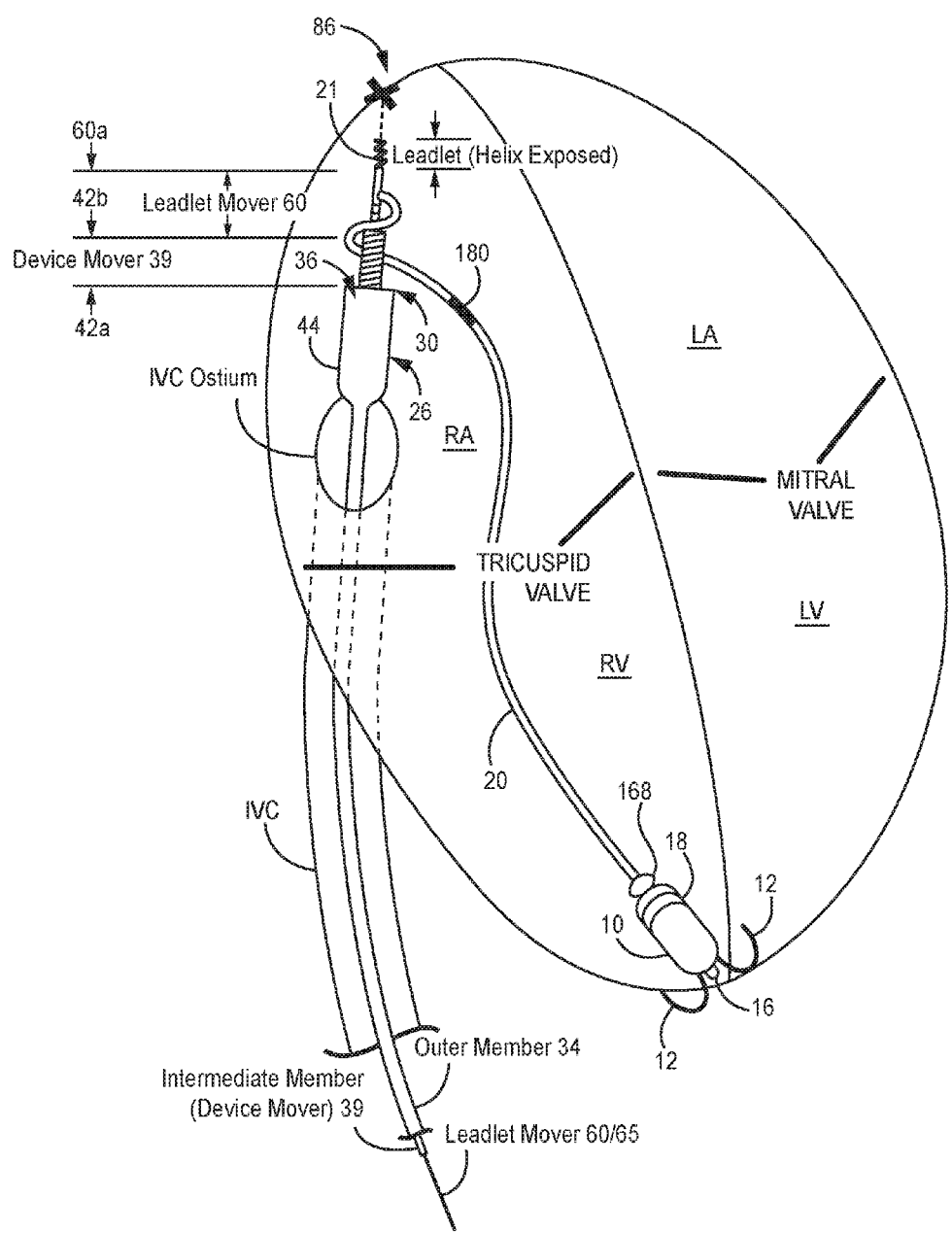
FIG. 11 is a schematic view of a leadlet that has been counter-rotated and can be advanced to a fixation point onto cardiac tissue.
Figure 12:
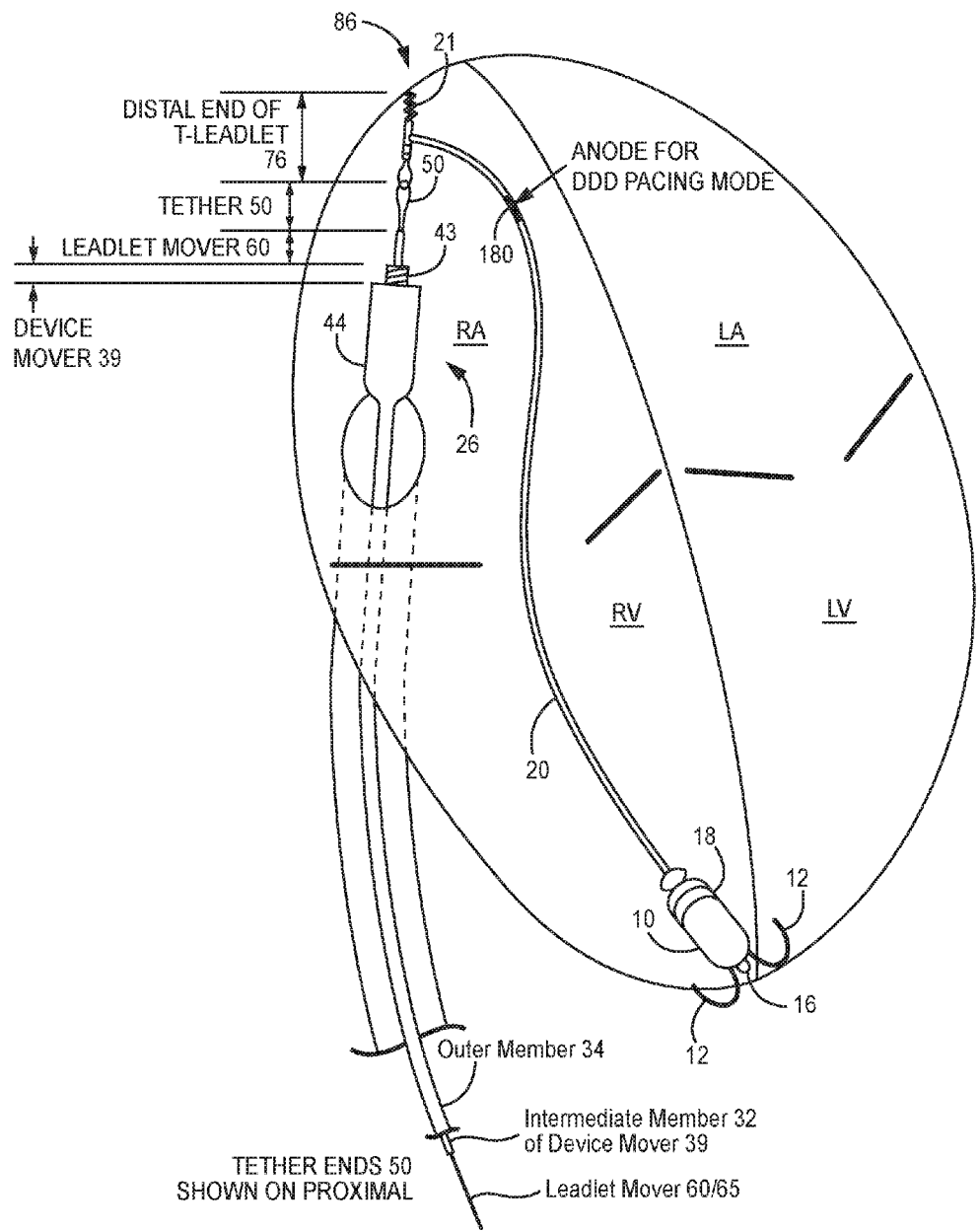
FIG. 12 is a schematic view depicting the leadlet and device mover after the leadlet has been fixated and before retracting the leadlet and device movers.

FIG. 10 is a flow diagram of method 200 related to attaching a leadlet to atrial appendage tissue as shown and described relative to FIGS. 11-12. Exemplary leadlets that can be employed herein include leadlet 20 and leadlet 300 described below; however, it should be appreciated that other leadlet designs may also be able to be used.

Before implementing method 200, as previously discussed, LPD 10 is attached to cardiac tissue such as the left and/or the right ventricular tissue. For example, one or more LPD 10 can be placed in the left ventricle, the right ventricle or both ventricles. As previously stated, ventricular portion 88 is typically deployed by advancing the delivery device 26 through a venous system of the patient, for example, from a femoral venous access site and up through an inferior vena cava (IVC) of the patient into RA and across the tricuspid valve into right ventricle RV, until a distal end 30 of delivery device 26 abuts the target implant site. With distal end 30 abutting the implant site, the user applies a push force through delivery device 26 while retracting outer member 34 to release fixation tines 12 of ventricular portion 88 out through distal opening 36 (FIG. 4A) for engagement with tissue at the implant site. The user checks the electrical response to delivered paces to the ventricular tissue. If the response is determined to effectively capture tissue, the user proceeds to position deliver device 26 such that the distal opening 36 of outer member 34 shown in FIG. 3B is directed into an atrium.

At block 202, the leadlet helix 21 is deployed. In particular, the leadlet helix 21 is moved distally until it extends out of the leadlet mover 60 from delivery device 26. At block 204, a part of the leadlet body 23 is positioned into one side of the groove or slot 66. The helix 21 is centered within the forks 64 so that leadlet 20 is locked into position in leadlet mover 60 shown in FIG. 8A. The user may be able to feel or hear leadlet 20 contact proximal end 71 of leadlet mover 60. Once leadlet 20 is substantially or actually locked into position, leadlet 20 can be torqued by the leadlet mover 60. Leadlet 20 is torqued by counter-rotating leadlet 20 around the leadlet mover 60 as shown in FIG. 11. Counter-rotation of leadlet 20 occurs by moving, in a counter clockwise motion, the free end near helix 21 of the leadlet 20. Counter-rotation of leadlet 20 causes the leadlet 20 to wrap or twist around the leadlet mover 60 so that the leadlet 20 and the leadlet mover 60 look like a red-striped barber pole or candy cane. The leadlet 20 is rotated a number of times around the leadlet mover 60. For example, the leadlet 60 can be counter-rotated up to three or four times. The leadlet and leadlet mover are then deemed to be in a counter-rotated state. Counter-rotated means the leadlet is rotated in a counter clockwise direction.

At block 206, the leadlet 20 is moved or advanced to the atrial wall. For example, the device mover 39 is located between points 42a,b while leadlet mover 60 advances from point 42 to point 60a. The user can place the helix 21 directly onto atrial tissue. For example, the user can place the helix 21 onto atrial tissue near or at atrial appendage 38 such that helix 21 abuts against pectinate muscle (PM).

At block 208, the leadlet 20 is rotated by the leadlet mover 60. The rotation of the leadlet 20 causes the helical tip 21 to gradually attach to tissue thereby fixating the helical tip 21 to the atrial wall. Under fluoroscopy, the user can view through the programmer user interface the unwinding of the leadlet 20. Unwinding of the leadlet indicates that a rotation has occurred. Once the leadlet 20 is unwound, the helix 21 is attached to the wall. The helix 21 can be further rotated in a clockwise direction by the user rotating control member 9.

FIG. 12 shows retraction of the leadlet mover 60 and device mover 39 to perform a tug test to determine effectiveness of the physical attachment between the helix 21 and atrial tissue. Electrical testing is also performed to determine the electrical stimulation through the conductor of leadlet 20 to the helix 21 captures the tissue. If the electrical stimulation is sufficient, the tether is removed or loosened at block 210. The tether is loosened by opening the Tuohy-Borst valve 95 (FIGS. 9A-9B) thereby opening port 94b. Tuohy-Borst valve 95 is located near luer lock 99 and flush line 97. At block 212, the delivery device 26 retraces its movement to exit the heart.

Method 200 is different compared to conventional methods that torque leadlets. For example, counter-rotation to wind leadlet 20 followed by rotating the leadlet 20 to unwind the leadlet 20 in order to attach helix 21 to atrial appendage tissue is the complete opposite of the steps employed by conventional Medtronic, Inc. helical leads. For example, Medtronic, Inc. helical leads typically are wound by rotating of the leadlet body or lead mover member followed by counter-rotation of the leadlet body to relieve any residual torque to attach the lead to tissue.

Figure 21:
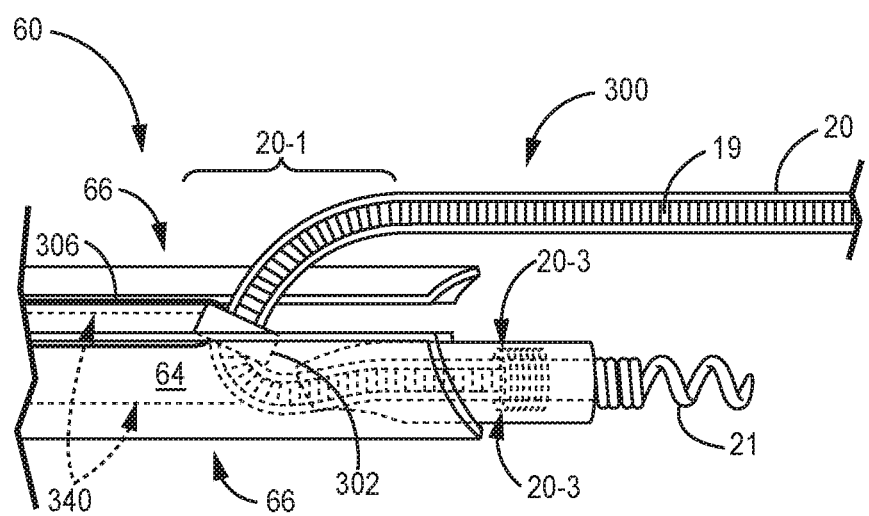
FIG. 21 depicts a schematic view of the second leadlet embodiment of FIG. 20 in which the leadlet is moved in a more proximal position in the lumen of the leadlet mover and one side of the leadlet is locatable in the slot of the leadlet mover.
Figure 22:
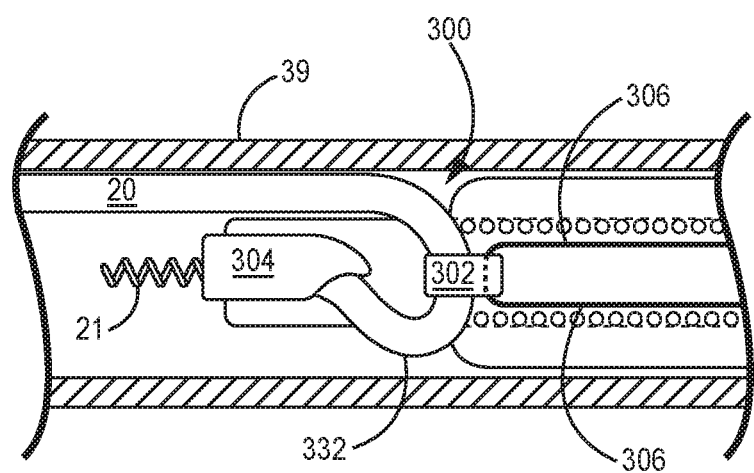
FIG. 22 depicts a schematic view of the second leadlet embodiment of FIG. 21 in which the leadlet is folded onto itself inside a lumen of the leadlet mover.
Figure 23:
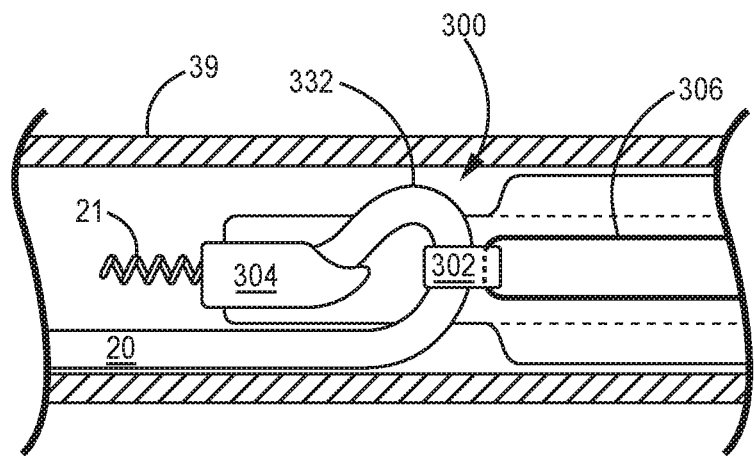
FIG. 23 depicts a schematic view of the second leadlet embodiment in which the leadlet is folded onto itself inside a lumen of the leadlet mover.
Figure 24:
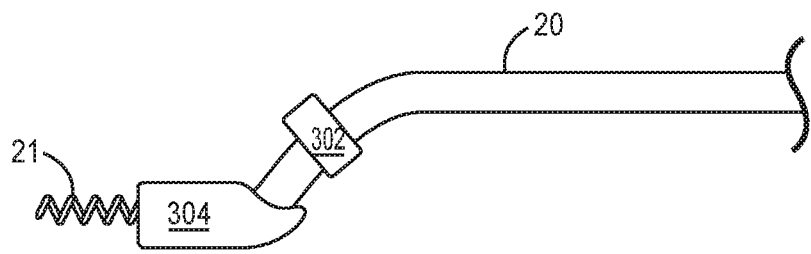
FIG. 24 depicts a schematic view of the second leadlet embodiment shown in FIG. 23 after the leadlet exited the leadlet mover.

Referring to FIGS. 13-25, a second leadlet embodiment 300 is disclosed that can be used in cooperation with delivery device 26 to deliver the LPD 10 to a first tissue site (e.g. ventricular tissue) and then deliver the leadlet 300 to a second tissue site (e.g. atrial tissue) using method 200. The second leadlet 300 embodiment comprises a leadlet body 23, a sleeve head 304 to connect the leadlet body 23 (FIG. 14), a core 325 that connects the conductor 19 to a fixation component (e.g. helix 21 etc.), coil 322 (providing mechanical support) and a ring 302 around the leadlet body 23. The sleeve head 304 is configured to connect with leadlet body 20. Sleeve head 304 extends a length of about 3 mm and has a diameter of about 1.65 mm that is slightly greater than the lead body 20 to allow the tip to center in the forks of the leadlet mover 60. The bend/taper 334 of the sleeve head 304 forces the leadlet body 23 to enter the forks 64 of leadlet mover 60 or cup, formed by forks 64, while the user pulls on the tethers to pull ring 302 into the lumen. While entering the cup in region 20-1 and 20-2 of FIG. 20 of the leadlet mover 60, the sleeve head 304 serves as a "bumper" that may contact the inner diameter 340 of the cup formed by forks 64 while positioning the leadlet 300 therein. Referring to FIG. 21, only the leadlet head 350, starting at proximal position 20-3 of head 350 fits between the inner surfaces of forks 64. FIGS. 20-21 depict leadlet 300 disposed in deliver device 26.

Figure 19:
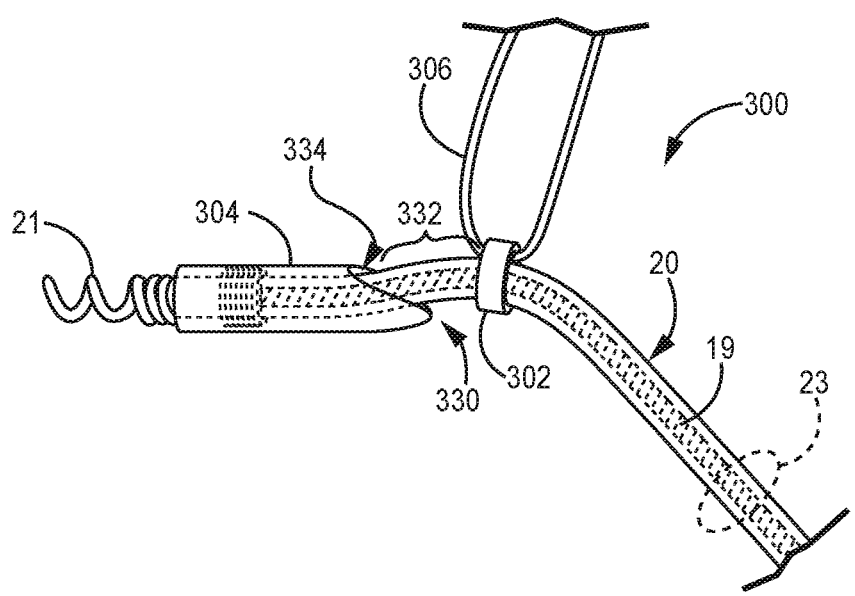
FIG. 19 depicts a schematic view of the second leadlet embodiment of FIGS. 13-17.

The ring 302 is configured to provide sufficient space between the lead body 20 and the inner diameter of ring 302 to allow a tether 306 to loop therebetween. The ring 302 and tether 306 functions in a similar way as a nose ring in a bull. Just as the nose ring can be used to pull and control the bull, the ring 302 and tether 50 control movement of the leadlet 300. The tether 306 is about 180 degrees from sleeve head bend 334 for orienting the leadlet 300 to move the leadlet 300 into the delivery device 26. Sleeve head 304 is connected to leadlet body 20. Referring to FIG. 19, at the distal end of leadlet body 20 includes a flexible section 332 that allows the leadlet body 20 to bend. Flexible section 332 is configured to bend or move after the tether has been attached to the ring 302. Ring 302 can comprise a non-conductive polymer or a conductive metal which can double as an electrode (i.e. sense ring) that is coupled to a conductor in the leadlet body.

The leadlet 300, positioned near the distal end of the delivery device 26, as shown in FIGS. 20-24, is pulled through the distal opening 36 and into the lumen of delivery device 26 until the ring 302 is seated at shelf 332 of delivery device 26. After the user has been able to pull ring 302 near to shelf 332, first portion 20-1 is folded over second portion 20-2 of leadlet body 20 in a U-shape configuration shown in FIG. 20.

Figure 25A:
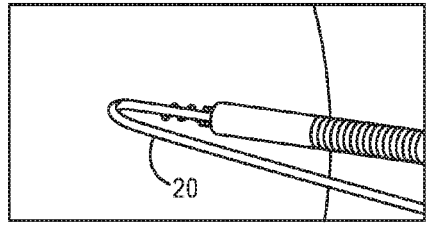
FIG. 25A depicts a schematic view of the second leadlet embodiment in which the helical tip extends outside a sheath.
Figure 25H:
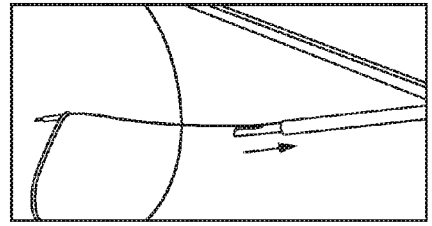
FIG. 25H depicts a schematic view of the leadlet mover and delivery device positioned in still a more proximal position relative to FIG. 25G while the leadlet remains fixated in position.
Figure 25B:
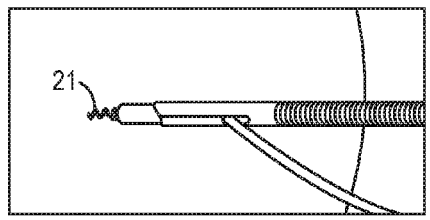
FIG. 25B depicts a schematic view of the leadlet body, shown in FIG. 25A, dropping outside of the groove or slot of a leadlet mover.
Figure 25G:
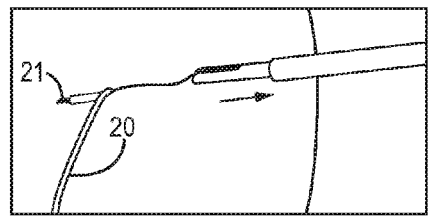
FIG. 25G depicts a schematic view of the leadlet mover and delivery device positioned in a more proximal position relative to FIG. 25F while the leadlet remains fixated in position.
Figure 25C:
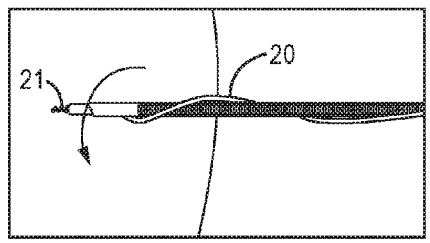
FIG. 25C depicts a schematic view of the leadlet body, shown in FIG. 25B, in which the leadlet body is counter-rotated around the leadlet mover.
Figure 25F:
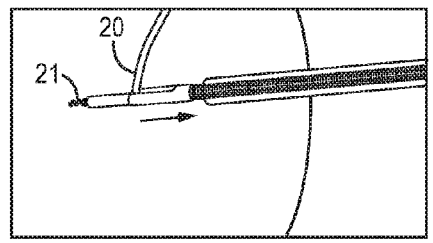
FIG. 25F depicts a schematic view of the leadlet mover and delivery device being retracted while the leadlet remains fixated in position.
Figure 25D:
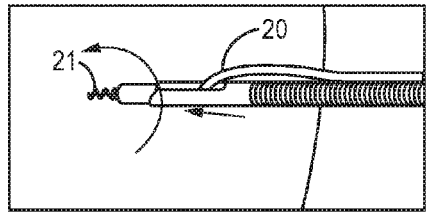
FIG. 25D depicts a schematic view of the leadlet attaching tissue, shown in FIG. 25B, by rotating the helical tip.
Figure 25E:
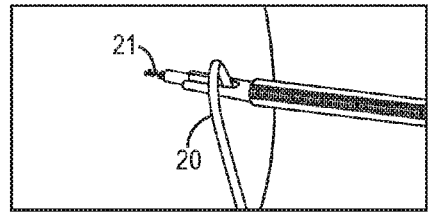
FIG. 25E depicts a schematic view of the helical tip attached to the auger shown in FIG. 25D.

FIGS. 25A-25H depicts details between leadlet 300 attaching tissue FIG. 25A includes leadlet 300 in which the helical tip 21 extends from the leadlet mover (also referred to as a sheath). In one or more embodiments shown in FIGS. 25E-25H the leadlet mover coil (described earlier) is replaced with a polymer tube. In this case, the tubing incorporates a radiopaque additive to help the physician see the tubing location. FIG. 25B depicts the leadlet body 20 dropping outside the groove or slot 66 (shown FIGS. 8A-8B) of the leadlet mover 60. FIG. 25C shows the leadlet body 20 counter-rotated around the leadlet mover 60. The leadlet body 20 is typically counter-rotated three or four times around the leadlet mover 60. FIG. 25D shows leadlet 300 attaching to auger by rotating the helical tip 21. FIG. 25E is shows the helical tip 21 is attached to tissue. FIG. 25F depicts the leadlet mover 60 and delivery device 26 being retracted while leadlet 300 remains fixated in position. FIG. 25G depicts the leadlet mover 60 and delivery device 26 positioned in a more proximal position relative to FIG. 25F while leadlet 300 remains fixated in position. FIG. 25H depicts the leadlet mover 60 and delivery device 26 positioned in still a more proximal position relative to FIG. 25G while leadlet 300 remains fixated in position. Leadlet 300 would be in its relaxed or more natural state if the lead body in FIG. 24, or 25F or 25G was more straight.

Figure 26A:
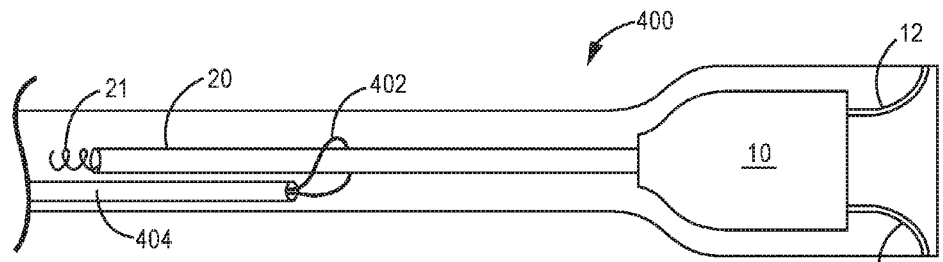
FIG. 26A is a schematic view of a delivery device for placing a pacing device having active tines.

FIGS. 26A-26E depict numerous leadlet delivery device systems that may be used to attach leadlet 20 to cardiac tissue (e.g. atrial tissue) using method 200 incorporated herein. Each embodiment in FIGS. 26A-26E can be configured to operate in the same fashion as outlined in method 200 except as described below. FIG. 26A depicts a delivery system 400 that comprises pacing device 10, delivery element 404, tether 402 extending from delivery element 404, leadlet 20 with an active helix 21. Delivery element 404 and tether 402 are pre-loaded to loop around leadlet 20. Once leadlet 20 is attached to tissue, tether 402 can be cut and delivery device 26 removed.

Figure 26B:
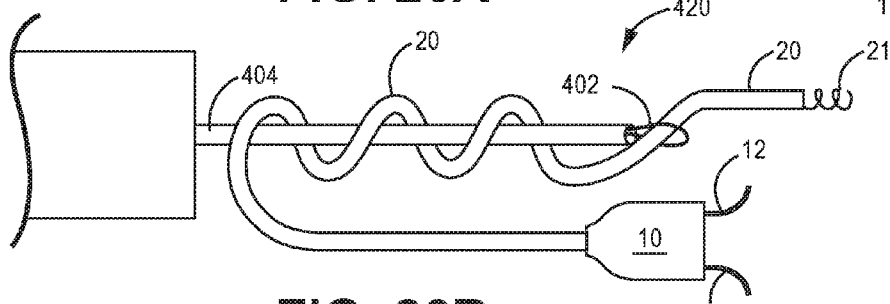
FIG. 26B is a schematic view of another active delivery device system.

Delivery system 420, shown in FIG. 26B, includes a pacing device 10, delivery element 404, tether 402 extending from delivery element 404, and leadlet 20 with an active helix 21. In this embodiment, the leadlet 20 is twisted around the delivery element 404. The leadlet 20 is then positioned near tissue. The leadlet body then unwinds thereby attaching the helix 21 to tissue. Tether 402 is then loosened.

Figure 26C:
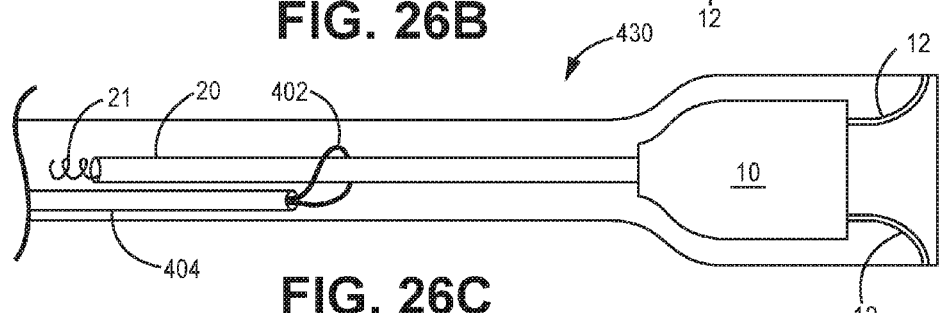
FIG. 26C is a schematic view of another version of a delivery device.

FIG. 26C depicts a delivery system 430 that comprises pacing device 10, delivery element 404, tether 402 extending from delivery element 404, leadlet 20 with an active helix 21. Delivery element 404 and tether 402 are pre-loaded to loop around leadlet 20. Once leadlet 20 is attached to tissue, tether 402 can be cut and delivery device 26 removed.

Figure 26D:
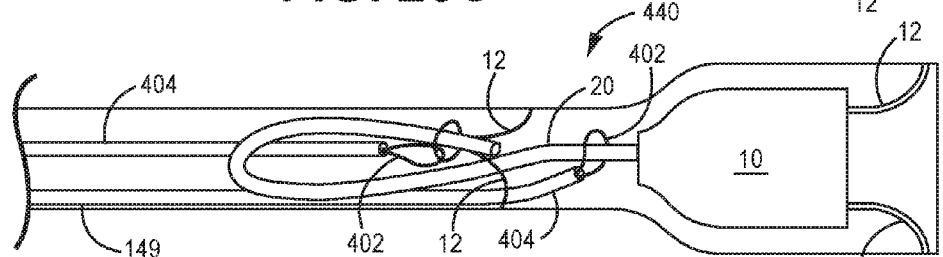
FIG. 26D is a schematic view of a leadlet that loops back onto itself and pulled within the cup of a delivery device system.

FIG. 26D depicts a delivery system 440 that includes a set of tines 12 at the end of the leadlet 20. Outside the end of the leadlet 20 is a loop configured to connect with a tether. The tether wraps around the loop 78. The tether loop connection is used to hold onto the other loop, which is similar to a person holding a handle to a bucket. The tether centers the pacing device 10. Once centered, the pacing device 10 is moved inside the delivery device 26. The user pulls on the single tether, located at the proximal end, to load the device 10 into the delivery device 26. The user continues to pull on the single tether until the tines 12 drop in or enter the device cup 44.

Figure 26E:
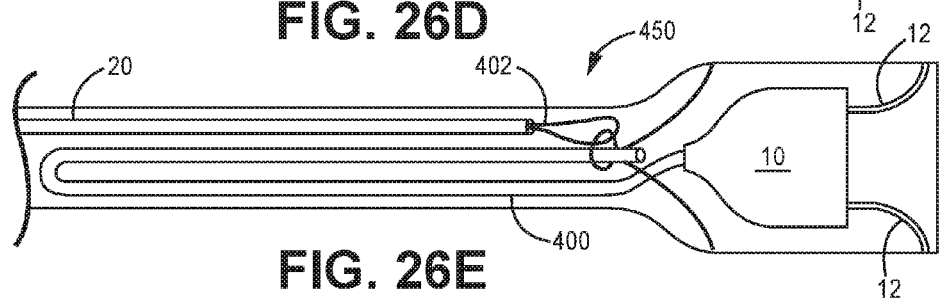
FIG. 26E is a schematic view of yet another delivery device embodiment.

FIG. 26E depicts a delivery system 450 includes a set of passive tines 12 at the end of the leadlet 20. Outside the end of the leadlet 20 is a loop configured to connect with a tether. The tether wraps around the loop 78. The tether loop connection is used to hold onto the loop, which is similar to a person holding a handle to a bucket. The tether centers the pacing device 10. Once centered, the pacing device 10 is moved inside the delivery device 26. The user pulls on the single tether, located at the proximal end, to load the device 10 into the delivery device 26. The user continues to pull on the single tether until the tines 12 drop in or enter the device cup 44.

Skilled artisans appreciate that except for the tines directly attached to LPD 10, passive tines can be used in place of the helix on the leadlets shown on each embodiment in FIGS. 26A-26E. Passive tines generally float in the atria until snagging occurs between the passive tines and the pectinate muscle. Passive tines are not actively puncture the pectinate muscle like the active tines of LPD 10.

Figure 13:
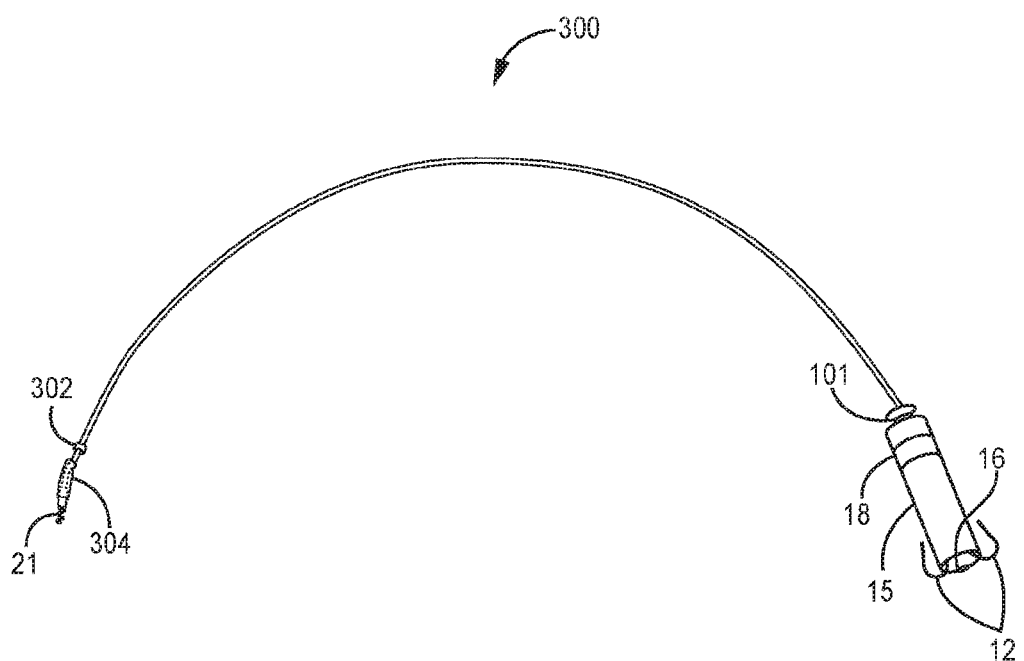
FIG. 13 is a schematic view that depicts a pacing device with a second leadlet embodiment (i.e. hooped leadlet) that has a ring loop to couple with a tether for repositioning the leadlet.

In the foregoing detailed description, specific exemplary embodiments have been described. However, it may be appreciated that various modifications and changes can be made without departing from the scope of the invention as set forth below. Many different embodiments exist relative to the present disclosure. For example, while FIGS. 1, 12-13 depict the LPD 10 placed in the RV and the leadlet 20 positioned at the atrial appendage, LPD 10 can be placed in or on the LV, RA or LA. Similarly, leadlet 20 can be placed in various locations in the heart such as the LV, RV, or LA. Optionally, leadlet 20 can include a ring electrode to allow tip to ring bipolar pacing and/or sensing.

One alternative embodiment relates to the leadlet guide 170. While leadlet guide 170 is shown attached to leadlet 20, leadlet guide 170 can also be configured to be positioned and fixated at the distal end of the delivery device 26. In this embodiment, the used aligns the leadlet into the leadlet guide 170.

Another alternative embodiment relates to bipolar sensing electrodes can integrated bipolar (tip-to-coil) for other device 8 configurations.

A snare-type tool, such as is known to those skilled in the art, may be employed in lieu of tether 50, such that the term "tether" may broadly refer to such a snare.

In one or more embodiments, intermediate member 32, including a coiled distal end 43, shown in FIG. 4A, can be configured to engage device ventricular portion 88 by abutting distal end 43.

SUMMARY OF ILLUSTRATIVE EMBODIMENTS

The following paragraphs enumerated consecutively from 1 through 29 provide for various aspects of the present invention. In one embodiment, in a first paragraph (1), the present invention provides a method for using a delivery device to position a leadlet pacing device (LPD) in cardiac tissue, the delivery device comprising a proximal end, a distal end and a lumen extending therebetween sized to receive the LPD, the LPD having a leadlet with a fixation device extending therefrom, the method comprising:

(a) introducing the LPD into the distal end of the delivery device and the leadlet extending proximally from the LPD while the fixation device extends distally toward the LPD;

(b) advancing the LPD out of the delivery device using a LPD mover;

(c) advancing the leadlet out of the delivery device using a leadlet mover;

(d) rotating the leadlet mover after advancing the leadlet out of the delivery device, wherein rotation of the leadlet mover results in counter-rotating of the leadlet around the leadlet mover to a counter rotated state; and (e) releasing the leadlet from the counter-rotated state to cause the fixation device of the leadlet to rotate and engage the fixation device of the leadlet with cardiac tissue.

Embodiment 2

The method of embodiment 1 wherein the leadlet comprises a proximal end and a distal end, the proximal end comprising a leadlet body and a distal end comprising a T-shape.

Embodiment 3

The method of any of embodiments 1 or 2 wherein the leadlet mover is configured to rotate the leadlet through a slotted end.

Embodiment 4

The method of any of embodiments 1-3 wherein the cardiac tissue comprises atrial appendage tissue.

Embodiment 5

The method of any of embodiments 1-4 further comprising:
(g) loosening a tether; and
(h) in response to loosening the tether, retracting the delivery device.

Embodiment 6

A method of any of embodiments 1-5 wherein the leadlet mover comprises a coil portion and a wire portion.

Embodiment 7

A method of any of embodiments 1-6 wherein the fixation device is configured to perform one of pacing and sensing.

Embodiment 8

A method of any of embodiments 1-7 further comprising: delivering a device that includes a second electrode.

Embodiment 9

A method of any of embodiments 1-8 further comprising: pacing using one or more modes comprising DDD mode or VDD mode.

Embodiment 10

A method of any of embodiments 1-9 wherein the T-shape distal end of the leadlet is configured to allow the leadlet body to move into a tubular portion of the leadlet mover.

Embodiment 11

A method of any of embodiments 1-10 wherein the tububular portion comprises a set of slots.

Embodiment 12

A method of any of embodiments 1-11 wherein the T-shaped leadlet distal design allows the leadlet body to fold back onto itself while loaded in the delivery device such that the leadlet body does not interfere with the fixation device when the fixation device is located outside of a delivery device cup.

Embodiment 13

A method of any of embodiments 1-12 wherein the leadlet comprises a hooped leadlet.

Embodiment 14

A delivery device to position a leadlet pacing device (LPD) in cardiac tissue, the delivery device comprising a proximal end, a distal end and a lumen extending therebetween, the LPD having a leadlet extending therefrom, the leadlet comprising a fixation device, the delivery device comprising:
(a) an introducer to introduce the LPD into the delivery device such that the LPD is loaded in the distal end of the delivery device and the leadlet extends proximally from the LPD while the fixation device extends distally toward the LPD;
(b) a LPD mover configured to advance the LPD out of the delivery device; and
(c) a rotatable leadlet mover, wherein the leadlet mover comprises a portion engageable with the leadlet body such that rotation of the leadlet mover results in counter-rotating of the leadlet around the leadlet mover to a counter rotated state until the leadlet is released from the counter-rotated state to cause the fixation device of the leadlet to rotate and engage the fixation device of the leadlet with cardiac tissue.

Embodiment 15

The delivery device of embodiment 14 wherein the leadlet comprises a proximal end and a distal end, the distal end comprising a T-shape.

Embodiment 16

The delivery device of any of embodiments 14-15 wherein the T-shape distal end is configured to allow the leadlet body to move into a slotted tube portion of the leadlet mover.

Embodiment 17

The delivery device of any of embodiments 14-16 wherein the T-shaped leadlet distal design allows the leadlet body to fold back onto itself while loaded in the delivery device such that the leadlet body does not interfere with the fixation device when the fixation device is located outside of a delivery device cup.

Embodiment 18

A delivery device of any of embodiments 14-17 wherein the leadlet mover comprises a slotted tubular portion configured to engage with the leadlet body.

Embodiment 19

A delivery device of any of embodiments 14-18 wherein the leadlet mover further comprises coil portion and a wire portion.

Embodiment 20

A delivery device of any of embodiments 14-19 wherein the fixation device of the leadlet comprises a helix.

Embodiment 21

A delivery device of any of embodiments 14-20 wherein the leadlet comprises a hooped leadlet.

Embodiment 22

A delivery device of any of embodiments 14-21 wherein the hooped leadlet comprises a leadlet body with a ring configured to encircle the leadlet body.

Embodiment 23

A delivery device of any of embodiments 14-22 further comprising a tether configured to be positioned between the leadlet body and an inner surface of the ring.

Embodiment 24

A delivery device of any of embodiments 14-23 wherein the tether is configured to pull the leadlet body into a lumen of the delivery device.

Embodiment 25

A delivery device of any of embodiments 14-24 wherein in response to the fixation device being fixated to tissue, the leadlet is in a relaxed state to cause the fixation device of the leadlet to rotate and engage the fixation device.

Embodiment 26

The delivery device of any of embodiments 14-25 wherein the helix is a right handed pitch helix.

Embodiment 27

A delivery device of any of embodiments 14-27 wherein the leadlet body is wound around the leadlet mover.

Embodiment 28

A method for using a delivery device to position a leadlet pacing device (LPD) in cardiac tissue, the delivery device comprising a proximal end, a distal end and a lumen extending therebetween sized to receive the LPD, the LPD having a leadlet with a fixation device extending therefrom, the method comprising:
(a) introducing the LPD into the distal end of the delivery device and the leadlet extending proximally from the LPD while the fixation device extends distally toward the LPD;
(b) advancing the LPD out of the delivery device using a LPD mover;
(c) advancing the leadlet out of the delivery device using a leadlet mover;
(d) counter-rotating the leadlet around the leadlet mover as the leadlet mover for a counter-rotated state after advancing the leadlet out of the delivery device;
(e) using the leadlet mover to cause the leadlet to engage with cardiac tissue in response to counter-rotating the leadlet; and
(f) rotating the leadlet to attach the fixation device to the cardiac tissue.

Embodiment 29

A delivery device to position a leadlet pacing device (LPD) in cardiac tissue, the delivery device comprising a proximal end, a distal end and a lumen extending therebetween, the LPD having a leadlet extending therefrom, the leadlet comprising a fixation device, the delivery device comprising:
(a) an introducer to introduce the LPD into the delivery device such that the LPD is loaded in the distal end of the delivery device and the leadlet extends proximally from the LPD while the fixation device extends distally toward the LPD;
(b) a LPD mover configured to advance the LPD out of the delivery device; and
(c) a leadlet mover, wherein the leadlet mover comprises a portion engageable with the leadlet body such that the leadlet mover releases a leadlet having passive fixation tines that are configured to attach to pectinate muscle.

The present disclosure provides a more efficient single delivery device 26 solution to contain, deliver and attach both the leadlet 20 and the LPD 10 to separate tissue sites. The single delivery device 26 is more efficient than conventional delivery devices in at least two ways. First, the single delivery device 26 reduces costs over conventional devices that require two separate delivery devices to deliver a LPD and a leadlet with an electrode to the atria. Second, the single delivery device more quickly and efficiently delivers the LPD and the leadlet than conventional devices.

We claim:

1. A method for using a delivery device to position a leadlet pacing device (LPD) in cardiac tissue, the delivery device comprising a proximal end, a distal end and a lumen extending therebetween sized to receive the LPD, the LPD having a leadlet with a fixation device extending therefrom, the method comprising:
    (a) introducing the LPD into the distal end of the delivery device and the leadlet extending proximally from the LPD while the fixation device extends distally toward the LPD;
    (b) advancing the LPD out of the delivery device using a LPD mover;
    (c) advancing the leadlet out of the delivery device using a leadlet mover;
    (d) rotating the leadlet mover after advancing the leadlet out of the delivery device, wherein rotation of the leadlet mover results in counter-rotating of the leadlet around the leadlet mover to a counter rotated state; and
    (e) releasing the leadlet from the counter-rotated state to cause the fixation device of the leadlet to rotate and engage the fixation device of the leadlet with cardiac tissue.

2. The method of claim 1 wherein the leadlet comprises a proximal end and a distal end, the proximal end comprising a leadlet body and a distal end comprising a T-shape.

3. The method of claim 1 wherein the leadlet mover is configured to rotate the leadlet through a slotted end.

4. The method of claim 1 wherein the cardiac tissue comprises atrial appendage tissue.

5. The method of claim 4 further comprising:
    (g) loosening a tether; and
    (h) in response to loosening the tether, retracting the delivery device.

6. A method of claim 1 wherein the leadlet mover comprises a coil portion and a wire portion.

7. A method of claim 1 wherein the fixation device is configured to perform one of pacing and sensing.

8. A method of claim 1 further comprising:
    delivering a device that includes a second electrode.

9. A method of claim 8 further comprising:
    pacing using one or more modes comprising DDD mode or VDD mode.

10. A method of claim 2 wherein the T-shape distal end of the leadlet is configured to allow the leadlet body to move into a tubular portion of the leadlet mover.

11. A method of claim 10 wherein the tububular portion comprises a set of slots.

12. A method of claim 10 wherein the T-shaped leadlet distal design allows the leadlet body to fold back onto itself while loaded in the delivery device such that the leadlet body does not interfere with the fixation device when the fixation device is located outside of a delivery device cup.

13. A method of claim 1 wherein the leadlet comprises a hooped leadlet.

14. A delivery device to position a leadlet pacing device (LPD) in cardiac tissue, the delivery device comprising a proximal end, a distal end and a lumen extending therebetween, the LPD having a leadlet extending therefrom, the leadlet comprising a fixation device, the delivery device comprising:
(a) an introducer to introduce the LPD into the delivery device such that the LPD is loaded in the distal end of the delivery device and the leadlet extends proximally from the LPD while the fixation device extends distally toward the LPD;
(b) a LPD mover configured to advance the LPD out of the delivery device; and
(c) a rotatable leadlet mover, wherein the leadlet mover comprises a portion engageable with the leadlet body such that rotation of the leadlet mover results in counter-rotating of the leadlet around the leadlet mover to a counter rotated state until the leadlet is released from the counter-rotated state to cause the fixation device of the leadlet to rotate and engage the fixation device of the leadlet with cardiac tissue.

15. The delivery device of claim 14 wherein the leadlet comprises a proximal end and a distal end, the distal end comprising a T-shape.

16. The delivery device of claim 15 wherein the T-shape distal end is configured to allow the leadlet body to move into a slotted tube portion of the leadlet mover.

17. The delivery device of claim 15 wherein the T-shaped leadlet distal end design allows the leadlet body to fold back onto itself while loaded in the delivery device such that the leadlet body does not interfere with the fixation device when the fixation device is located outside of a delivery device cup.

18. A delivery device of claim 14 wherein the leadlet mover comprises a slotted tubular portion configured to engage with the leadlet body.

19. A delivery device of claim 14 wherein the leadlet mover further comprises coil portion and a wire portion.

20. A delivery device of claim 14 wherein the fixation device of the leadlet comprises a helix.

21. A delivery device of claim 14 wherein the leadlet comprises a hooped leadlet.

22. A delivery device of claim 14 wherein the hooped leadlet comprises a leadlet body with a ring configured to encircle the leadlet body.

23. A delivery device of claim 22 further comprising a tether configured to be positioned between the leadlet body and an inner surface of the ring.

24. A delivery device of claim 23 wherein the tether is configured to pull the leadlet body into a lumen of the delivery device.

25. A delivery device of claim 14 wherein in response to the fixation device being fixated to tissue, the leadlet is in a relaxed state to cause the fixation device of the leadlet to rotate and engage the fixation device.

26. The delivery device of claim 20 wherein the helix is a right handed pitch helix.

27. A delivery device of claim 14 wherein the leadlet body is wound around the leadlet mover.

28. A method for using a delivery device to position a leadlet pacing device (LPD) in cardiac tissue, the delivery device comprising a proximal end, a distal end and a lumen extending therebetween sized to receive the LPD, the LPD having a leadlet with a fixation device extending therefrom, the method comprising:
(a) introducing the LPD into the distal end of the delivery device and the leadlet extending proximally from the LPD while the fixation device extends distally toward the LPD;
(b) advancing the LPD out of the delivery device using a LPD mover;
(c) advancing the leadlet out of the delivery device using a leadlet mover;
(d) counter-rotating the leadlet around the leadlet mover as the leadlet mover for a counter-rotated state after advancing the leadlet out of the delivery device;
(e) using the leadlet mover to cause the leadlet to engage with cardiac tissue in response to counter-rotating the leadlet; and
(f) rotating the leadlet to attach the fixation device to the cardiac tissue.

29. A delivery device to position a leadlet pacing device (LPD) in cardiac tissue, the delivery device comprising a proximal end, a distal end and a lumen extending therebetween, the LPD having a leadlet extending therefrom, the leadlet comprising a fixation device, the delivery device comprising:
(a) an introducer to introduce the LPD into the delivery device such that the LPD is loaded in the distal end of the delivery device and the leadlet extends proximally from the LPD while the fixation device extends distally toward the LPD;
(b) a LPD mover configured to advance the LPD out of the delivery device; and
(c) a leadlet mover, wherein the leadlet mover comprises a portion engageable with the leadlet body such that the leadlet mover releases a leadlet having passive fixation tines that are configured to attach to pectinate muscle.

* * * * *